United States Patent
Ito

(10) Patent No.: US 6,340,681 B1
(45) Date of Patent: Jan. 22, 2002

(54) 2-BENZIMIDAZOLYLAMINE COMPOUNDS AS ORL-1-RECEPTOR AGONISTS

(75) Inventor: Fumitaka Ito, Chita-gun (JP)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 09/606,921

(22) Filed: Jun. 29, 2000

Related U.S. Application Data

(63) Continuation of application No. PCT/IB99/01290, filed on Jul. 16, 1999.

(51) Int. Cl.$^7$ .................. C07D 401/04; C07D 405/14; C07D 40/14; A61K 31/454; A61K 25/04
(52) U.S. Cl. .............. 514/234.5; 514/322; 514/253.09; 514/258; 546/199; 544/364; 544/129; 544/256
(58) Field of Search ..................... 546/199; 514/322, 514/253.09, 234.5, 258; 544/364, 129, 256

(56) References Cited

PUBLICATIONS

Barlocco et al., The opioid–receptor–like 1 as a potential target for new analgesics, Eur. J. Med. Chem., 35:275–282, Jan. 2000.*
CAS printout for Soudijn et al., Feb. 1997.*
CAS printout for Modlt et al., Oct. 1997.*

* cited by examiner

Primary Examiner—Mukund J. Shah
Assistant Examiner—Hong Liu
(74) Attorney, Agent, or Firm—Peter C. Richardson; Paul H. Ginsburg; Elsa Djuardi

(57) ABSTRACT

A compound of the formula:

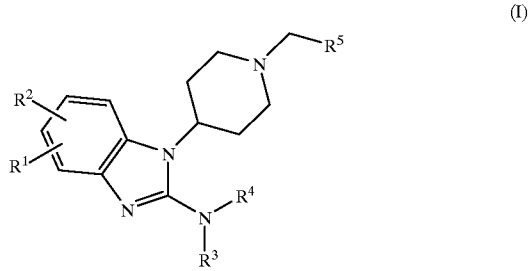

(I)

or a pharmaceutically acceptable salt thereof, wherein $R^1$ and $R^2$ are independently selected from hydrogen, halo, hydroxy, $(C_1–C_4)$alkyl, halo $(C_1–C_4)$alkyl and the like; $R^3$ and $R^4$ are independently selected from hydrogen, halo$(C_1–C_{10})$alkyl, optionally substituted $(C_1–C_6)$alkyl and the like, or $R^3$ and $R^4$, together with the nitrogen atom to which they are attached, form an optionally substituted fully saturated, partially saturated or fully unsaturated heterocyclic ring; and $R^5$ is $(C_4–C_{11})$cycloalkyl and the like, has ORL1-receptor agonist activity, and are useful as analgesics or the like in mammalian subjects.

10 Claims, No Drawings

2-BENZIMIDAZOLYLAMINE COMPOUNDS AS ORL-1-RECEPTOR AGONISTS

TECHNICAL FIELD

This application claims priority benefits under 35 U.S.C. § 365(a) of PCT/IB99/01290 filed Jul. 16, 1999.

This invention relates to novel 1-(substituted-piperidin-4-yl)-2-benzimidazolylamine compounds, and their salts, pharmaceutical compositions containing them and their medical uses. The compounds of this invention have activity as selective ORL1-receptor agonists, and as such are useful in treating or preventing disorders or medical conditions selected from pain, inflammatory diseases and the like.

BACKGROUND ART

In spite of their usefulness as analgesics, usage of opioids such as morphine and heroin are strictly limited. This is because these drugs induce side effects such as euphoria, respiratory failure, depression or constipation. Further, multiple dosage of the drugs may cause addiction. Thus, there has been a long-felt need to provide analgesics with reduced side effects.

From the above point of view, considerable pharmacological and biochemical studies have been carried out to identify opioid receptors and their endogenous ligands to prepare peptide and non-peptide opioid ligands for the receptors. In the recent past, amino acid sequences of mu- ($\mu$-), delta ($\delta$-) and kappa ($\kappa$-) opioid receptor subtypes have been identified and reported. Subsequently, a novel receptor subtype was identified and termed ORL1-receptor, and Meunier, J. -C et al. reported the isolation and structure of the endogenous agonist of the receptor (*Nature*, Vol. 377, pp. 532–535, Oct. 12, 1995). It is suggested that the agonist compounds for ORL1-receptor be effective in neurogenic inflammation (*Tips*, Vol. 18, pp. 293–300, August 1997). It is also suggested that the agonist compounds be potent analgesics having less psychological side effects and addiction (D. Julius, *Nature*, Vol. 377, p. 476, Oct. 12, 1995).

Neurosearch's WO 97/40035 discloses a 2-substituted 1-piperidyl benzimidazolyl compound substituted with a cycloalkyl group at the nitrogen atom of the piperidine group.

Novo Nordisk's WO 99/59997 discloses use of a small organic compound as an opioid receptor ligand for the treatment of a disease selected from migraine, non insulin dependent diabetes mellitus (type II diabetes), sepsis, inflammation, incontinence, vasomotor disturbances including the peripheral vasomotor effects such as hot flushes, and alleviating symptoms of drug withdrawal such as abstinence symptoms occurring during withdrawal from abusive drugs.

Schering Corporation's WO 00/06545 discloses use of a nociceptin receptor ORL1-agonist, alone or in combination with a second agent for treating pain, anxiety, asthma, depression, alcohol abuse, cough or allergy.

BRIEF DISCLOSURE OF THE INVENTION

The present invention provides a compound of the following formula:

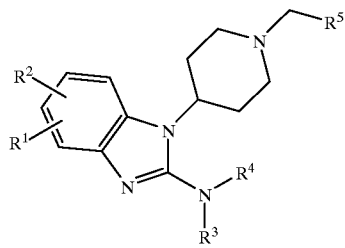

(I)

or a salt thereof wherein $R^3$ and $R^4$ are independently selected from hydrogen; halo($C_1$–$C_{10}$)alkyl;

($C_1$–$C_6$)alkyl optionally substituted with one to two substituents independently selected from hydroxy, ($C_1$–$C_4$)alkoxy, ($C_1$–$C_4$)alkyl-S—, phenoxy, amino, oxo, mono[($C_1$–$C_4$)alkyl]amino, di[($C_1$–$C_4$)alkyl]amino, N-[($C_7$–$C_9$)cycloalkyl-($C_1$–$C_4$)alkyl]-N-($C_1$–$C_4$)alkyl-amino, ($C_1$–$C_4$)alkoxy-C(=O)—, aryl selected from phenyl and naphtyl wherein the aryl is optionally substituted with one to three substituents independently selected from halo, hydroxy, ($C_1$–$C_4$) alkoxy and trifluoro($C_1$–$C_4$)alkoxy, and heterocyclyl selected from pyrrolidyl and piperidinyl wherein the heterocyclyl is optionally substituted with ($C_1$–$C_4$) alkyl;

($C_3$–$C_8$)cycloalkyl optionally substituted with ($C_1$–$C_4$) alkyl;

($C_3$–$C_8$)cycloalkenyl optionally substituted with ($C_1$–$C_4$)alkoxy-C(=O)—;

5- to 6-membered-heterocyclyl, 5- to 6-membered-heterocyclyl-C(=O)— and 5- to 6-membered-heterocyclyl-($C_1$–$C_4$)alkyl, wherein each heterocyclyl contains in the ring one to three heteroatoms independently selected from oxygen, nitrogen and sulfur, is optionally fused to a phenyl ring, and is optionally substituted with one to two substituents independently selected from halo, ($C_1$–$C_4$)alkyl, benzyl and oxo;

phenyl optionally substituted with one to three substituents independently selected from halo, ($C_1$–$C_4$) alkyl, halo($C_1$–$C_4$)alkyl and ($C_1$–$C_4$)alkoxy; and 5- to 6-membered heteroaryl-($C_1$–$C_4$)alkyl wherein said heteroaryl contains one to four ring atoms independently selected from oxygen, nitrogen and sulfur and is optionally fused to a phenyl ring; or $R^3$ and $R^4$, together with the nitrogen atom to which they are attached, form a fully saturated, partially saturated or fully unsaturated 5- to 8-membered nitrogen containing heterocyclic ring wherein said heterocyclic ring optionally contains in the ring one or two additional heteroatoms independently selected from nitrogen, oxygen and sulfur, optionally contains in the ring a group $CR^6R^7$ wherein $R^6$ and $R^7$ taken together form an oxo group or a cyclic acetal, and optionally fused to a phenyl, naphthalene or ($C_5$–$C_8$)cycloalkyl ring, and optionally substituted with one to two substituents independently selected from halo; ($C_1$–$C_4$)alkyl; halo ($C_1$–$C_4$)alkyl; ($C_1$–$C_4$)alkoxy; hydroxy; carbonyl; benzhydryl; hydroxy-($C_1$–$C_4$)alkyl; ($C_1$–$C_4$)alkoxy-($C_1$–$C_4$)alkyl-; amino; amino($C_1$–$C_4$)alkyl-amino-; mercapto; ($C_1$–$C_4$)alkoxy-C(=O)—; pyrrolidino-($C_1$–$C_4$)alkyl; amino-C(=O)—; ($C_1$–$C_4$)alkyl-C(=O)—; ($C_1$–$C_4$)alkoxy-C(=O)—amino-; piperidinyl optionally substituted with one or two substituents independently selected from amino, mono[($C_1$–$C_4$)alkyl]amino-, di[($C_1$–$C_4$)alkyl]amino-, benzylamino and di-(benzyl)amino; phenyl optionally substituted with one to three substituents independently selected from halo and ($C_1$–$C_4$)alkoxy, phenyl-($C_1$–$C_4$)alkyl; phenyl-($C_1$–$C_4$)alkenyl; phenyl-($C_1$–$C_4$)alkoxy-C(=O)—; 1,3-benzodioxolyl-($C_1$–$C_4$)alkyl-; trifluoromethyl; nitro; pyridyl optionally substituted with one to three substituents independently selected from halo and trifluoromethyl; quinolinyl optionally substituted with one to three substituents independently selected from halo and trifluoromethyl; pyrrolidinyl-($C_1$–$C_4$) alkyl; and pyrrolidinyl-$(CH_2)_m$—$CR^8R^9$—$(CH_2)_n$— wherein m and n are independently 1, 2, 3 or 4, and $R^8$ and $R^9$, taken together with the carbon atom to which they are attached, form ($C_3$–$C_6$)cycloalkyl; and $R^5$ is phenyl or ($C_4$–$C_{11}$)cycloalkyl optionally substituted with one to three substituents independently selected from the group consisting of hydrogen, halo, hydroxy, ($C_1$–$C_4$)alkyl, halo ($C_1$–$C_4$)alkyl, ($C_1$–$C_4$)alkoxy, ($C_1$–$C_4$)alkylsulfonyl, ($C_1$–$C_4$)alkyl-C(=O)—, carboxy, ($C_1$–$C_4$)alkyl-C(=O)O—, amino, $NH_2$—C(=O)—, ($C_1$–$C_4$)alkyl-C(=O)—NH—, ($C_1$–$C_4$)alkyl-$SO_2$—NH—, phenyl and naphthyl.

This invention also relates to a pharmaceutical composition for the treatment of a disorder or condition mediated by ORL1-receptor and its endogenous ligands in a mammal including a human, or for anesthetizing a mammal including a human, which comprises an effective amount of the compound of formula (I) as defined above, or a pharmaceutically acceptable salt thereof, and a pharmaceutically acceptable carrier.

This invention also relates to a method of treating a disorder or condition, or anesthetizing a mammal including a human, the treatment and anesthetization of which can be effected or facilitated by agonising ORL1-receptor in a mammal including a human, comprising administering to a mammal in need of such treatment an effective amount of a compound of formula (I) or a pharmaceutically acceptable salt thereof.

DETAILED DESCRIPTION OF THE INVENTION

The term "alkyl", as used herein, means a straight or branched saturated monovalent hydrocarbon radical including, but not limited to, methyl, ethyl, propyl, isopropyl, n-butyl, sec-butyl, tert-butyl and the like.

The term "cycloalkyl", as used herein, means a saturated carbocyclic radical including, but not limited to, cyclopropyl, cyclobutyl, cyclohexyl, cycloheptyl, cyclooctyl, cyclononyl, cyclodecyl and the like.

The term "alkoxy", as used herein, means an O-alkyl group wherein "alkyl" is defined above.

The term "halo", as used herein, refers to F, Cl, Br or I, preferably F or Cl.

The term "heterocyclyl", as used herein, unless otherwise indicated, includes a non-aromatic and optionally bridged heterocyclic-group having 5 to 8 atoms comprising 1 to 4 heteroatoms each selected from oxygen (O), sulfur (S) and nitrogen (N). Examples of the heterocyclic include pyrrolidino, piperidino, morpholino, piperazinyl, homopiperidinyl and homopiperazinyl.

The term "heteroaryl", as used herein, unless otherwise indicated, refers to a monocyclic aromatic hydrocarbon group having five to six ring atoms comprising one to four heteroatoms each independently selected from N, O and S. Examples of the heteroaryl include furyl, thiophenyl, pyrrolyl, pyrazolyl, imidazolyl, triazolyl, tetrazolyl, isoxazolyl, oxazolyl, thiazolyl, isothiazolyl, oxadiazolyl, pyridyl, pyridazinyl, pyrimidinyl, pyrazinyl, triazinyl, indolyl, benzofuranyl, benzothiophenyl, isoindolyl and isobenzofuranyl.

The term "treating", as used herein, refers to reversing, alleviating, inhibiting the progress of, or preventing the disorder or condition to which such term applies, or one or more symptoms of such disorder or condition. The term "treatment" as used herein refers to the act of treating, as "treating" is defined immediately above.

A preferred group of compounds of the present invention includes those compounds of formula (I) wherein $R^1$ and $R^2$ are independently selected from hydrogen, halo, ($C_1$–$C_4$)alkyl, ($C_2$–$C_4$)alkenyl, ($C_2$–$C_4$)alkynyl, halo($C_1$–$C_4$)alkyl and ($C_1$–$C_4$)alkoxy;

$R^3$ and $R^4$ are independently selected from hydrogen; halo($C_1$–$C_{10}$)alkyl; ($C_1$–$C_6$)alkyl optionally substituted with one to two substituents independently selected from hydroxy, ($C_1$–$C_4$)alkoxy, phenoxy, amino, mono [($C_1$–$C_4$)alkyl]amino, di[($C_1$–$C_4$)alkyl]amino, phenyl and naphthyl; ($C_3$–$C_8$)cycloalkyl; 5- to 6-membered heterocyclyl-($C_1$–$C_4$)alkyl wherein said heterocyclyl is selected from pyrrolidino, piperidino, morpholino, piperazinyl and homopiperazinyl, and optionally substituted with one to two substituents independently selected from halo and oxo; phenyl optionally substituted with one to three substituents independently selected from halo, ($C_1$–$C_4$)alkyl, halo($C_1$–$C_4$)alkyl and ($C_1$–$C_4$)alkoxy; and heteroaryl-($C_1$–$C_4$)alkyl wherein said heteroaryl is selected from furyl, thiophenyl, pyrrolyl, pyrazolyl, imidazolyl, triazolyl, tetrazolyl, isoxazolyl, oxazolyl, thiazolyl, isothiazolyl, oxadiazolyl, pyridyl, pyridazinyl, pyrimidinyl, pyrazinyl, triazinyl, indolyl, benzofuranyl, benzothiophenyl, isoindolyl and isobenzofuranyl; and $R^5$ is unsubstituted ($C_4$–$C_{11}$)cycloalkyl.

More preferred compounds of this invention are those compounds of formula (I), wherein $R^1$ and $R^2$ are independently selected from hydrogen; halo; ($C_1$–$C_4$)alkyl; ($C_2$–$C_4$)alkenyl; ($C_2$–$C_4$)alkynyl; halo($C_1$–$C_4$)alkyl and ($C_1$–$C_4$)alkoxy;

$R^3$ and $R^4$ are independently selected from hydrogen; halo($C_1$–$C_{10}$)alkyl; ($C_1$–$C_6$)alkyl optionally substituted with one to two substituents independently selected from hydroxy, ($C_1$–$C_4$)alkoxy, phenoxy, amino, mono [($C_1$–$C_4$)alkyl]amino, di[($C_1$–$C_4$)alkyl]amino, phenyl and naphthyl; ($C_3$–$C_8$)cycloalkyl; heterocyclyl-($C_1$–$C_4$)alkyl wherein said heterocyclyl is selected from pyrrolidino, piperidino, morpholino, piperazinyl and homopiperazinyl, and optionally substituted with one to two substituents independently selected from halo and oxo; phenyl optionally substituted with one to three substituents independently selected from halo, ($C_1$–$C_4$)alkyl, halo($C_1$–$C_4$)alkyl and ($C_1$–$C_4$)alkoxy; and heteroaryl-($C_1$–$C_4$)alkyl wherein said heteroaryl is selected from furyl, thiophenyl, pyrrolyl, pyrazolyl, imidazolyl, triazolyl, tetrazolyl, isoxazolyl, oxazolyl, thiazolyl, isothiazolyl, oxadiazolyl, pyridyl, pyridazinyl, pyrimidinyl, pyrazinyl, triazinyl, indolyl, benzofuranyl, benzothiophenyl, isoindolyl and isobenzofuranyl; and $R^5$ is unsubstituted ($C_4$–$C_{11}$,)cycloalkyl.

More preferred compounds of this invention are those compounds of formula (I), wherein $R^1$ and $R^2$ are both hydrogen;

$R^3$ and $R^4$ are independently selected from hydrogen, $(C_1-C_6)$alkyl optionally substituted with one to three substituents independently selected from hydroxy, $(C_1-C_4)$alkoxy, phenoxy, di[$(C_1-C_4)$alkyl]amino, phenyl and naphthyl; $(C_3-C_8)$cycloalkyl; heterocyclyl-$(C_1-C_4)$alkyl wherein said heterocyclyl is selected from pyrrolidino, piperidino, morpholino and piperazinyl, and optionally substituted with one to two substituents independently selected from halo and oxo; phenyl optionally substituted with one to three halo; and heteroaryl-$(C_1-C_4)$alkyl wherein said heteroaryl is selected from furyl, pyridyl and indolyl; and $R^5$ is unsubstituted $(C_5-C_8)$cycloalkyl.

More preferred compounds of this invention are those compounds of formula (I) wherein $R^1$ and $R^2$ are both hydrogen; $R^3$ and $R^4$ are independently selected from hydrogen and $(C_1-C_6)$alkyl optionally substituted with one to three substituents independently selected from hydroxy, $(C_1-C_4)$alkoxy, phenoxy, di-[$(C_1-C_4)$alkyl]amino, phenyl and naphthyl; and $R^5$ is unsubstituted $(C_5-C_8)$cycloalkyl.

A specific preferred compound of this invention is N-cyclohexyl-1-[1-(cyclooctylmethyl)-4-piperidinyl]-1H-benzimidazol-2-amine, or a salt thereof.

Another preferred group of compounds of the present invention includes compounds of formula (I) wherein, $R^1$ and $R^2$ are independently selected from hydrogen, halo, $(C_1-C_4)$alkyl, $(C_2-C_4)$alkenyl, $(C_2-C_4)$alkynyl, halo$(C_1-C_4)$alkyl and $(C_1-C_4)$alkoxy;

$R^3$ and $R^4$, together with the nitrogen atom to which they are attached, form a 5- to 6-membered heterocyclic ring selected from pyrrolidino; piperidino; morpholino; piperazinyl and homopiperazinyl, and optionally substituted with one to two substituents independently selected from $(C_1-C_4)$alkyl, hydroxy, hydroxy-$(C_1-C_4)$alkyl, amino, amino-$(C_1-C_4)$alkyl, and piperidinyl optionally substituted with one or two substituents independently selected from amino, benzylamino, di-(benzyl)amino, $(C_1-C_4)$alkyl-C(=O)— and pyrrolidino-$(CH_2)_m$—$CR^7R^8$—$(CH_2)_n$—, wherein m and n are independently 1, 2, 3 or 4, and $R^7$ and $R^8$, taken together with the carbon atom to which they are attached, form $(C_3-C_6)$cycloalkyl; and $R^5$ is unsubstituted $(C_4-C_{11})$cycloalkyl.

More preferred compounds of this invention are those compounds of formula (I), wherein $R^1$ and $R^2$ are both hydrogen;

$R^3$ and $R^4$, together with the nitrogen atom to which they are attached, form a 5- to 6-membered heterocyclic ring selected from pyrrolidino; piperidino; morpholino; and piperazinyl optionally substituted with one to two substituents independently selected from $(C_1-C_4)$alkyl, hydroxy, hydroxy-$(C_1-C_4)$alkyl, amino, amino-$(C_1-C_4)$alkyl, $(C_1-C_4)$alkyl-C(=O)— and piperidinyl optionally substituted with one or two substituents independently selected from amino, benzylamino, di-(benzyl)amino and pyrrolidino-$(CH_2)_m$—$CR^7R^8$—$(CH_2)_n$—, wherein m and n are independently 1, 2, 3 or 4, and $R^7$ and $R^8$, taken together with the carbon atom to which they are attached, form $(C_3-C_6)$cycloalkyl; and $R^5$ is unsubstituted $(C_5-C_8)$cycloalkyl.

More preferred compounds of this invention are those compounds of formula (I), wherein $R^1$ and $R^2$ are both hydrogen; $R^3$ and $R^4$, together with the nitrogen atom to which they are attached, form piperazinyl substituted with $(C_1-C_4)$alkyl; and $R^5$ is unsubstituted $(C_5-C_8)$cycloalkyl.

Specific preferred compounds of this invention include 1-(1-cyclooctylmethyl-4-piperidinyl)-2-(4-methylpiperazinyl)-1H-benzimidazole; 1-(1-cyclohexylmethyl-4-piperidinyl)-2-(4-methylpiperazinyl)-1H-benzimidazole; and 1-(1-Cycloheptylmethyl-4-piperidinyl)-2-(4-methylpiperazinyl)-1H-benzimidazole; or a salt thereof.

Accordingly, this invention relates to a pharmaceutical composition for the treatment of a disorder or condition mediated by ORL1-receptor and its endogenous ligands in a mammal including a human, or for anesthetizing a mammal including a human, which comprises an effective amount of the compound of formula (I), or a pharmaceutically acceptable salt thereof, and a pharmaceutically acceptable carrier.

More specifically, this invention relates to a pharmaceutical composition for the treatment of a disorder or condition selected from the group consisting of inflammatory diseases, inflammation-related hyperalgesia, eating disorders, arterial blood pressure disorders, tolerance to narcotic analgesics, dependence on narcotic analgesics, anxiety, stress disorders, psychic trauma, schizophrenia, Parkinson's disease, chorea, depressant, Alzheimer's disease, dementias, epilepsy, convulsions, migraine, non insulin dependent diabetes mellitus (type II diabetes), sepsis, incontinence, vasomotor disturbances including the peripheral vasomotor including hot flushes, alleviating symptoms of drug withdrawal including abstinence symptoms occurring during withdrawal from abusive drugs, anxiety, asthma, alcohol abuse, cough and allegy; useful as analgesics, anesthetics, neuroprotective agents or analgesic enhancers; or useful for controlling water balance, hearing regulation, controlling sodium ion excretion or ameliorating brain function, comprising an amount of a compound of formula (I), or a pharmaceutically acceptable salt thereof that is effective in treating such disorder or condition, or effective in the use in a mammal including a human, and a pharmaceutically acceptable carrier.

This invention also relates to a method of treating a disorder or condition, or anesthetizing a mammal including a human, where the treatment or anesthetization of which can be effected or facilitated by agonising ORL1-receptor in a mammal, including a human, comprising administering to a mammal in need of such treatment an effective amount of a compound of formula (I) or a pharmaceutically acceptable salt thereof.

More specifically, this invention relates to a method for treating a disorder or condition in a mammal including a human, where the disorder or condition is selected from the group consisting of inflammatory diseases, inflammation-related hyperalgesia, eating disorder (e.g., in obesity), arterial blood pressure disorders (i.e., hypertension or hypotension), tolerance to narcotic analgesics such as morphine, dependence on narcotic analgesics such as morphine, anxiety, stress disorders, psychic trauma, schizophrenia, Parkinson's disease, chorea, depressant, Alzheimer's disease, dementias, epilepsy and convulsions, or for anesthetizing a mammal including a human, or for alleviating pain (e.g., acute, chronic and neuropathic pain), producing a neuroprotective effect, enhancing analgesic, controlling water balance (e.g., in diabetes insipidus and polyuria), hearing regulation, controlling sodium ion excretion or ameliorating brain function in a mammal including a human, comprising administering to said mammal an effective amount of a compound of formula (I) or a pharmaceutically acceptable salt thereof and a pharmaceutically acceptable carrier.

This invention also relates to a pharmaceutical composition comprising a compound of formula (I) or a salt thereof in combination with a second agent for treating cough, allergy or asthma symptoms, specifically cough.

Examples of the second agent are antihistamines such as astemizole, azatadine, azelastin, acrivastin, brompheniramine, certirizine, cjloropheniramine, clemastine, cyclizine, carebastine, cyproheptadine, carbinoxamine, descarboethoxyloratadine, doxylamine, dimethindene, ebastine, epinastin, efletirizine, fexofenadine, hydroxyzine, ketotifen, lorotadine, levocabastine, mizolastine, equitazine, mianserin, noberastine, meclizine, norastemizole, picumast, pyrilamine, promethazine, terfenadine, tripelennarnine, temelastine, trimeplazine and triprolidine; histamine $H_3$-receptor antagonists such as thioperamide, imprormidine, burimamide, clobenpropit, impentamine, mifetidine, S-sopromidine, R-sopromidine, SKF-91486, GR-175737, GT-2016, UCL-1199 and clozapine; leukotriene inhibitors such as montelkast[R-(E)]-1[[[1-[3-[2-(7-chloro-2-quinolyl)-ethenyl]phenyl]-3-[2-(1-hydroxy-1-methylethyl)phenyl]propyl]thio]methyl] cyclopropaneacetic acid and its sodium salt, 1-((R)-(3-(2-(6,7-difluoro-2-quinolinyl)ethenyl)phenyl)-3-(2-(2-hydroxy-2-propyl)phenyl)thio)methylchclopropaneacetic acid and its sodium salt, 1-(((1(R)-3-(2-(2,3-dichlorothieno[3,2-b]pyridin-5-yl)-(E)-ethenyl)phenyl-3-(2-(1-hydroxy-1-methylethyl)phenyl)propyl)thio)methyl)cyclopropaneacetic acid and its sodium salt, pranlukast, N-[4-oxo-2-(1H-tetrazol-5-yl)-4H-benzopyran-8-yl]-p-(4-phenylbutoxy) benzamide), zafirlukast, (cyclopentyl-3-[2-methoxy-4-[(o-tolylsulfonyl)carbamoyl]benzyl]-1-methylindole-5-carbamate, and [2-[[2(4-tert-butyl-2-thiazolyl)-5-benzofuranyl]oxymethyl]phenyl]acetic acid; 5-lipoxygenase inhibitors such as zileuton, docebenone, pripost, ICI-D2318 and ABT761; β-adrenergic receptor agonists such as albuterol, bitolterol, isoetharine, mataproterenol, perbuterol, salmeterol, terbutaline, isoproterenol, ephedrine and epinephrine; a xanthine derivative such as theophylline; α-adrenergic receptor agonists such as arylalkylamines (e.g., phenylpropanolamine and pseudephedrine), imidazoles (e.g., naphazoline, oxymetazoline, tetrahydrozoline and xylometazoline) and cycloalkylamines (e.g., propylhexedrine); a mast sell stabilizer such as nedocromil sodium; anti-tussive agents such as codeine, dextromethorphan, benzonatate, chlophedianol and noscapine; an expectorant such as guaifenesin; NK1-, NK2- or NK3-tachykinin receptor antagonists such as CP-99,994 and SR 48968; and $GABA_B$ agonists such as baclofen and 3-aminopropyl-phosphinic acid.

General Synthesis

The following reaction Schemes illustrate the preparation of the compounds of the present invention. Unless otherwise indicated $R^1$ to $R^8$ in the reaction Schemes and discussion that follow are defined as above.

The ORL1 agonist compounds of Formula (I) of this invention may be prepared according to the following methods.

In a desired reaction step of the processes described hereafter, amino protections and removal of the amino protecting groups with reactants and reagents used may be carried out according to known procedures such as those described in Protective Groups in Organic Synthesis edited by T. W. Greene et al. (John Wiely & Sons, 1991). Typical amino protecting groups include benzyl, $C_2H_5CO_2$— and t-ButCO$_2$— represented as t-Boc or Boc.

Scheme 1 illustrates an embodiment of preparation process for a compound of formula (I).

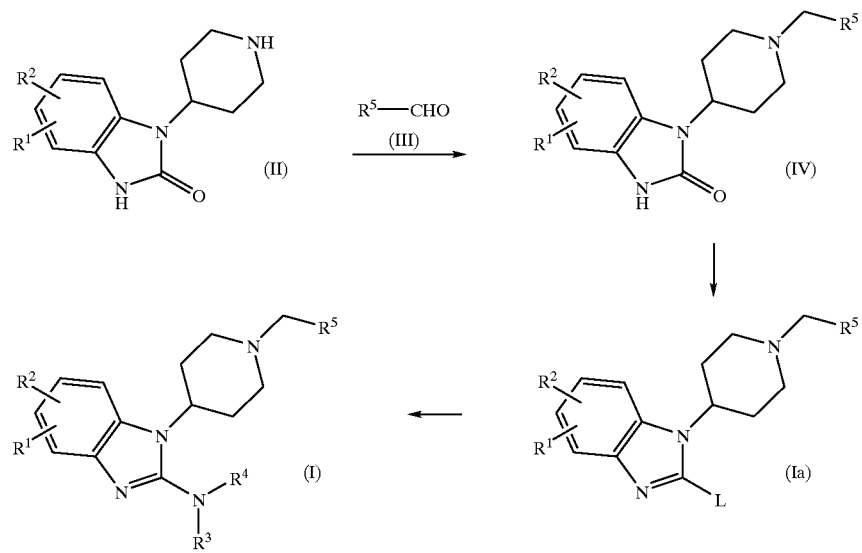

Scheme 1

As shown in Scheme 1, a compound of formula (I) via a compound of formula (Ia), wherein L represents a leaving group such as halo, may be obtained from benzimidazolylpiperidine compound of formula (II) via intermediate compound of formula (IV).

First, a compound formula (II) may be subjected to a reductive amination with an aldehyde compound of formula (III) to give the compound of formula (IV). Second, the compound of formula (IV) may be reacted with a suitable nucleophilic reagent to yield the compound of formula (Ia) by introducing a leaving group to the compound of formula (IV) in the presence or absence of a catalyst. Then, the compound of formula (Ia) may be subjected to a nucleophilic aromatic substitution reaction with an amino nucleophile to give the compound of formula (I).

The reductive amination of a compound of formula (II) may be carried out using a suitable hydride reagent to give the compound of formula (IV). A suitable hydride reagent is a boron-based mild reducing reagent such as $NaBH(OAc)_3$ or $NaBH_3CN$. This reaction can be carried out in a reaction inert solvent such as THF, $ClCH_2CH_2Cl$ or $CH_2Cl_2$ at about room temperature for from about 1 to about 48 hours.

The compound of formula (IV) thus obtained may be refluxed with a suitable nucleophilic reagent to give the compound of formula (Ia). In case of L is Cl, a suitable chlorinating reagent is, for example, phosphoryl chloride ($POCl_3$), phosphorus pentachloride ($PCl_5$) or phosgene ($COCl_2$)-triphenylphosphine ($Ph_3P$). In case of L is Br, a suitable bromination reagent is, for example, $Br_2$—$Ph_3P$. The brominaton may be carried out in a reaction inert solvent such as acetonitrile or DMF. The chlorination may be carried out under conditions for example reported by R. Iemura et al. *J. Med. Chem.* Vol. 29, pp. 1178–1183, 1986.

The nucleophilic aromatic substitution reaction of the compound of formula (Ia) to give the compound of formula (I) may be carried out according to a known enamine formation procedure in the presence or absence of a base. Suitable bases include Hünig base (i.e., diisopropylethylamine) and inorganic bases such as $K_2CO_3$. This reaction may be carried out in a reaction inert solvent at from about 0° to about 200° C. (preferably from 0° to 150° C.) for about 1 to about 24 hours (preferably from about 2 to about 12 hours). Suitable reaction inert solvents include alcohols such as methanol, ethanol, isopropyl alcohol, tert-butyl alcohol, and N,N-dimethylformamide (DMF) and the like. If appropriate, this reaction may be carried out in a suitable reaction chamber such as an autoclave.

A substitution reaction of a compound of formula (Ia) wherein L is Cl with an imide may also be carried out according to the procedures reported by C. H. Senanayake, et al., *Tetrahedron Lett.*, Vol. 38, pp. 5607–5610, 1997. In the report, Pd-catalyst is used in the presence of a base in toluene with heating.

A compound of formula (I) may be also prepared by subjecting a compound of formula (II) according to the preparation process illustrated in Scheme 2 comprising introduction of a leaving group, enamine formation and reductive amination.

Scheme 2

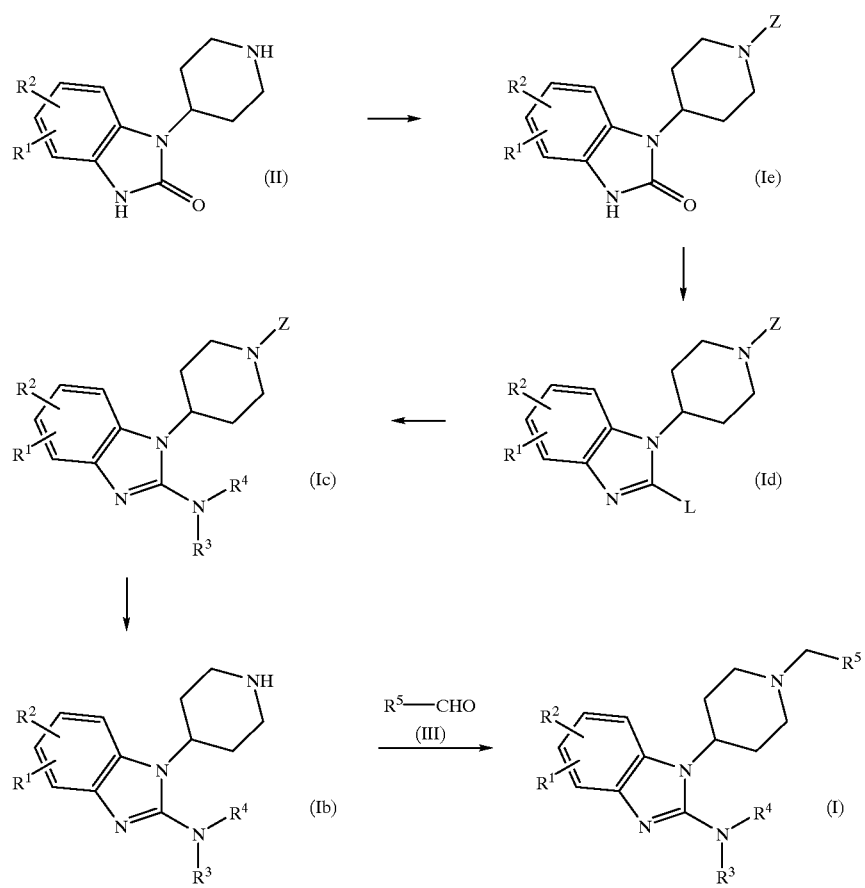

In the preparation process, first the piperidine group in a compound of formula (II) may be masked with a suitable amino-protecting group represented by Z. Suitable amino-protecting groups are benzyl-type protecting groups such as benzyl group. Benzyl group may conveniently be introduced to the compounds of formula (II) in the presence of NaBH(OAc)$_3$ or K$_2$CO$_3$ in DMF and removed by hydrogenolysis over Pd/C. Subsequent steps comprising leaving group introduction, enamine formation and reductive amination may be carried out according to the procedures illustrated in Scheme 1.

An intermediate compound of formula (IV) may be also prepared according to the procedure illustrated in Scheme 3.

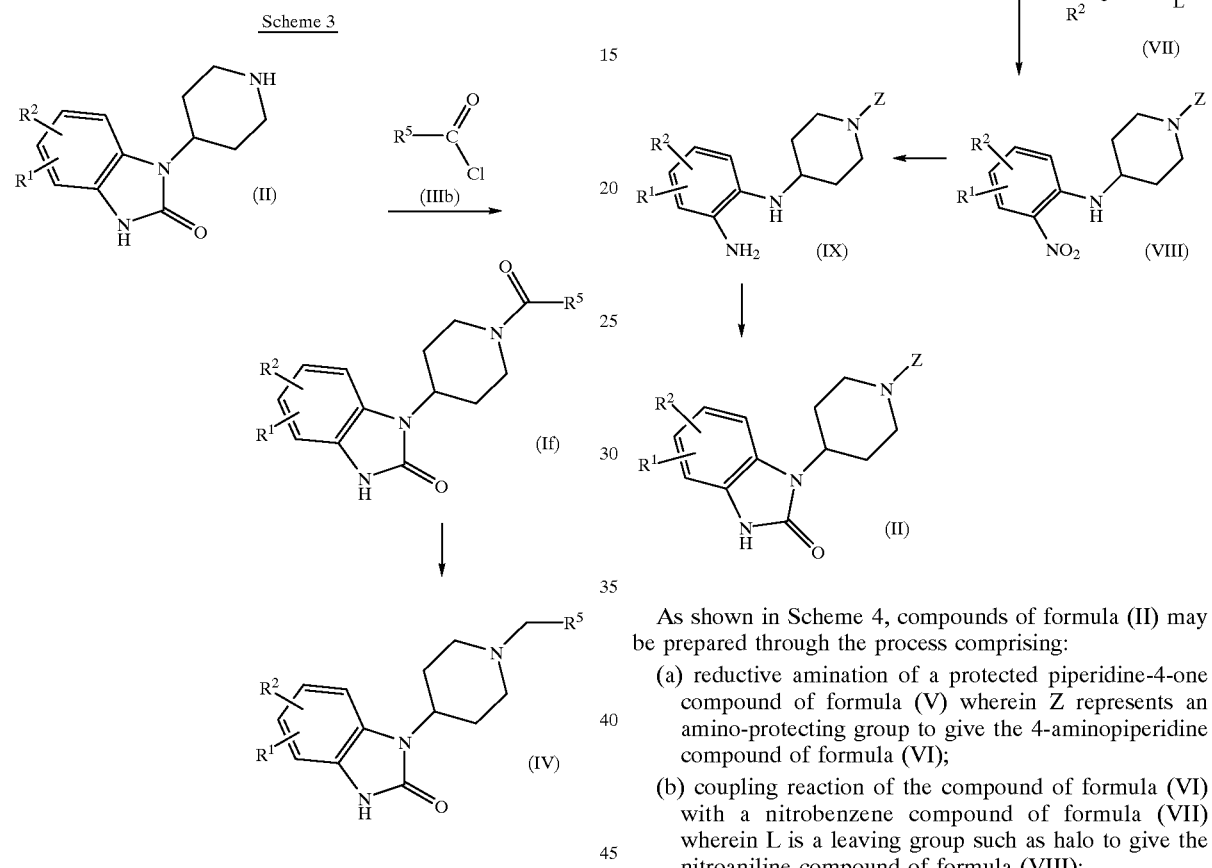

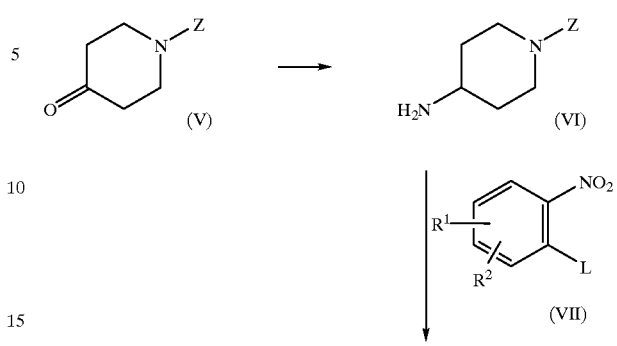

A compound of formula (II) may be coupled with a carbonyl chloride compound of formula (IIIb) to give the amide compound of formula (If) then reduced to the compound of formula (IV). The former coupling reaction may be carried out in the presence of a base such as triethylamine in a reaction inert solvent such as dichloromethane (CH$_2$Cl$_2$). Suitable reaction temperature ranges from 0° to 40° C., preferably at about 0° C. Suitable reaction time ranges from about 30 minutes to about 48 hours, preferably from about 1 to about 24 hours. The latter reduction may be carried out in the presence of a reducing reagent such as LiAlH$_4$ in a reaction inert solvent such as THF. Suitable reaction temperature ranges from about −78° to about 20° C., preferably from about −30° to about 0° C.

Starting from an amino-protected piperidine-4-one compound of formula (V), a compound of formula (II) may be prepared via carbonylation of an intermediate diamine compound of formula (V) according to the procedures illustrated in Scheme 4.

As shown in Scheme 4, compounds of formula (II) may be prepared through the process comprising:
(a) reductive amination of a protected piperidine-4-one compound of formula (V) wherein Z represents an amino-protecting group to give the 4-aminopiperidine compound of formula (VI);
(b) coupling reaction of the compound of formula (VI) with a nitrobenzene compound of formula (VII) wherein L is a leaving group such as halo to give the nitroaniline compound of formula (VIII);
(c) reduction of the resulting nitroaniline compound of formula (VIII) to give the diamine compound of formula (IX); and
(d) carbonylation of the compound of formula (IX) followed by removal of the amino protecting group to give the compound of formula (II)

Each reaction step is described more specifically in the following.
(a) The reductive amination may be conducted by an oximation of an amino-protected piperidine4-one compound of formula (V) followed by reduction. Both of the reactions may be conducted under conditions for oximation of carbonyl compounds known to those skilled in the art. For example, the oximation may be carried out by reacting the piperidine compound with hydroxylamine in the presence or absence of a base in a reaction inert solvent such as alcohol at about room temperature for about 0.5 to 48 hours. The resulting oxime compound may be extracted and subjected to reduction under known conditions to give the amine compound of formula (VI). The reduction may be carried out in the presence of a reducing reagent such as lithium aluminum hydride in a reaction inert solvent such as THF at about 0° C. to room temperature for from about 0.5 to 48 hours.

(b) & (C) Steps (b) and (c) may be carried out under conditions known to those skilled in the art (e.g., B. de Costa et al., *J. Chem. Soc. Perkin. Trans.*, Vol. 1, pp. 1671–1680, 1992 and N. A. Meanwell et al., *Bioorganic & Medicinal Chemistry Letters*, Vol. 6, No. 14, pp. 1641–1646, 1996). For example, coupling reaction (b) may be carried out in the presence of a base such as $K_2CO_3$ and triethylamine ($NEt_3$) in a reaction inert solvent such as acetonitrile under reflux for about 0.5 to 48 hours. Then, the resulting compound of formula (VIII) may be extracted and subjected to reduction to give the diamine compound of formula (IX). The reduction may be carried out in the presence of a suitable reducing reagent such as $SnCl_2$, zinc and iron in a reaction inert solvent such as ethanol at a temperature in the range from room temperature to the reflux temperature of the reaction mixture (preferably under reflux) for from about 0.5 to about 48 hours. The reduction may also be carried out under known hydrogenation conditions such as in the presence of a metal catalyst such as Raney nickel catalysts, palladium catalysts and platinum catalysts at a temperature in the range from about 0° to 100° C. (preferably at about room temperature) under hydrogen atmosphere in a reaction inert solvent such as ethanol or THF for from about 0.5 hours to 2 days.

(d) The carbonylation of the compound of formula (IX) may be carried out using a suitable carbonylating agent such as carbonyldiimidazole, trichloromethyl chloroformate, triphosgene or urea, in a reaction inert solvent such as THF, benzene, toluene or chloroform, at the temperature in the range of from about 0° to about 120° C. for from about 0.5 to about 24 hours. The reaction may be conducted according to the procedures described in WO 98/54168. Then, removal of the protecting group may be carried out according to procedures known to those skilled in the art to give the compound of formula (II).

In the above preparation process, benzyl-type amino protecting groups may conveniently be introduced to or removed from the compound according to the similar conditions illustrated with Scheme 2.

Alternatively, a compound of formula (IX) may be subjected to a coupling reaction with an isothiocyanate compound and a subsequent desulfurization under known conditions to give a compound of formula (1) wherein either $R^3$ or $R^4$ is hydrogen. For example, the first coupling reaction may be carried out in a reaction inert solvent such as an alcohol (e.g., ethanol) at from about room temperature to 100° C. from 30 minutes to 48 hours under stirring. The desulfurization may be carried out in the presence of an alkyl halide under reflux for from about 30 minutes to 48 hours.

A compound of formula (I) wherein $(R^3)(R^4)$N-group has an amino or an imino group (e.g., piperidinyl, piperazinyl and the like) at its terminal position may be further reacted with a desired reactant under known conditions to modify the Y. For example, these amine or imine compounds may be reacted with an alkylcarbonyl halide at about room temperature in a basic solvent to give an amide compound. The amine or imine compounds may be reacted with an amino acid, or an amino acid sulfone or sulfoxide in the presence or absence of a coupling reagent known to those skilled in the art in peptide synthesis. Suitable coupling reagents include WSC and the like. The amino or imino compound may be coupled with an amino acid, an amino acid sulfone or sulfoxide, or a phthalimido alkyl sulfonyl halide under conventional amide formation conditions in the presence of a coupling reagent in a reaction inert solvent such as acetonitrile at about room temperature. These amino acids include isoleucine, alanine, methionine, proline, phenylalanine, valine, and the like. Suitable coupling reagents are those typically used in peptide synthesis including WSC, dicyclohexylcarbodiimide (DCC), N,N'-carbonyldiimidazole (CDI), $POCl_3$, $TiCl_4$, $SO_2ClF$, benzotriazol-1-yl diethyl phosphate, $Ti(Obu)_4$, molecular sieves, N,N,N',N'-tetramethyl(succinimido)uronium tetrafluoroborate, CBMIT, Lawesson's reagent, chlorosulfonyl isocyanate, $P_2I_4$, pyridinium salts-$Bu_3N$, and a mixture of $Bu_3P$ and PhCNO. The amine or imine compounds may be also reacted with a guanidine compound under known conditions. A suitable reaction condition comprises reaction with an amino-protected guanidine compound in a reaction inert solvent such as THF at about room temperature (see M. S. Bematowicz, et al., *Tetrahedron Lett.*, Vol. 34, The starting materials (III), (IIIb), (V) and (IIV) and the other reactants are known or commercially available compounds, or may be prepared according to known procedures for a person skilled in the art.

Compounds of formula (I) of this invention may be prepared by either General Procedure A or B below.

General Procedure A:

A mixture of 2-chloro-1-(1-cyclooctylmethyl-4-piperidinyl)-1H-benzimidazole (36 mg, 0.1 mmol) and an appropriate amine compound (about 0.6 mmol) in DMSO (about 0.5 ml) is heated at about 135° C. for about 5 hrs. The volatiles are removed by $N_2$ blow. The residue is dissolved in $CH_2Cl_2$-EtOH (about 1 ml) and loaded onto a 0.2 g/2 ml Bond Elute (silica gel) eluting with $CH_2Cl_2$. The eluent is evaporated to dryness to give the product (judged by LC-MS). If necessary, the crude product is purified by LC-MS or preparative TLC ($CH_2Cl_2$-EtOH).

General Procedure B:

A mixture of 2-chlorobenzimidazole (18 mg, 0.05 mmol), an appropriate amine compound (about 0.3 mmol), and diisopropylethylamine (about 0.3 mmol) in toluene (about 0.3 ml) is heated at about 135° C. for about 5 hrs. Merrifield resin and piperazinomethyl resin are added to scavenge excess reagents. The filtrate is evaporated to give the product in good yield and purity (judged by LC-MS). If necessary, the crude product is purified by LC-MS or preparative TLC.

In the each reaction described above, unless indicated otherwise, the reaction pressure is not critical. Generally, the reactions will be conducted at a pressure of about one to about three atmospheres, preferably at ambient pressure (about one atmosphere).

The subject invention also includes isotopically-labelled compounds, which are identical to those recited in formula (I), but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^3$H and $^{14}$C are incorporated, are useful in drug and/or substrate tissue distribution assay. Tritiated, i.e., $^3$H, and carbon-14, i.e., $^{14}$C, isotopes are particularly preferred for their ease of presentation and detectability. Further, substitution with heavier isotopes such as deutrium, i.e., $^2$H, can afford therapeutic advantage resulting from greater metabolic stability, for example increased in vivo half-life or reduced dosage requirement and, hence, may be preferred in some circumstances. Isotopically labelled compounds of formula (I) of this invention and prodrugs thereof can generally be prepared by carrying out the procedure disclosed in above-disclosed Schemes and/or Examples and Preparations below, by submitting a readily available isotopically labelled reagent for a non-isotopically labelld reagent.

The compounds of Formula (I) of this invention are basic, therefore they will form acid-addition salts. All such salts are within the scope of this invention. However, it is necessary to use an acid addition salts which is pharmaceutically-acceptable for administration to a mammal. The acid-addition salts can be prepared by standard methods. For example, the salts may be prepared by contacting the basic compounds with acid in substantially equivalent proportions in water or an organic solvent such as methanol or ethanol, or a mixture thereof. The salts can be isolated by crystallization from or evaporation of the solvent. Typical salts which can be formed are the hydrochloride, nitrate, sulfate, bisulfate, phosphate, acetate, lactate, citrate, tartrate, succinate, maleate, fumarate, gluconate, saccharate, benzoate, methanesulfonate, ethanesulfonate, benzenesulfonate, p-toluenesulfonate, oxalate and pamoate (1,1'-methylene-bis-(2-hydroxy-3-naphtoate)) salts.

In addition, when the compounds of this invention form hydrates or solvates they are also within the scope of this invention.

The compounds of Formula (I) have been found to possess selective affinity for ORL1-receptors and ORL-1 receptor agonist activity. Thus, these compounds are useful as an analgesic, anti-inflammatory, diuretic, anesthetic, neuroprotective, anti-hypertensive and anti-anxiety agent, and the like, in mammalian subjects, especially humans in need of such agents. The affinity, agonist activities and analgesic activity can be demonstrated by the following tests respectively.

Selective Affinity for ORL1-receptors: ORL1-receptor Affinity:

The ORL1receptor binding affinity of the compounds of this invention are determined by the following procedures. Human ORL1receptor transfected HEK-293 cell membranes and wheat-germ agglutinin coated SPA beads are combined with 0.4 nM[$^3$H]nociceptin and unlabeled test compounds in 200 µl of 50 mM Hepes buffer pH7.4 containing 10 mM MgCl$_2$ and 1 mM EDTA. This mixture is incubated at room temperature (abbreviated as rt) for 30 min to 60 min. Non specific binding is determined by the addition of 1 µM nociceptin. Radioactivity is counted by Wallac 1450 MicroBeta.

µ-receptor Affinity:

The mu (µ) opioid receptor binding affinity of the compounds of this invention are determined by the following procedures. Human-mu opioid receptor transfected CHO-K1 cell membranes and wheat-germ agglutinin coated SPA beads are combined with 1.0 nM[$^3$H]DAMGO and unlabeled test compounds in 200 µl of 50 mM Hepes buffer pH7.4 containing 10 mM MgCl$_2$ and 1 mM EDTA. This mixture is incubated at rt for 30 min to 60 min. Non specific binding is determined by the addition of 1 µM DAMGO. Radioactivity was counted by Wallac 1450 MicroBeta.

κ-receptor Affinity:

The kappa (κ) opioid receptor binding affinity of the compounds of this invention are determined by the following procedures. Human kappa-opioid receptor transfected CHO-K1 cell membranes and wheat-germ agglutinin coated SPA beads are combined with 0.5nM[$^3$H]CI-977 and unlabeled test compounds in 200 µl of 50 mM Hepes buffer pH7.4 containing 10 mM MgCl$_2$ and 1 mM EDTA. This mixture is incubated at rt for 30 min to 60 min. Non specific binding is determined by the addition of 1 µM CI-977. Radio activity is counted by Wallac 1450 MicroBeta.

δ-receptor Affinity:

The delta (δ) opioid receptor binding affinity of the compounds of this invention are determined by the following procedures. Human delta opioid receptor transfected CHO-K1 cell membranes and wheat-germ agglutinin coated SPA beads are combined with 2.0 nM[$^3$H]DPDPE and unlabeled test compounds in 200 µl of 50 mM Hepes buffer pH7.4 containing 10 mM MgCl$_2$ and 1 mM EDTA. The assay is incubated at room temperature for 30 min to 60 min. Non specific binding are determined by the addition of 1 µM of each non-labeled ligands. Radioactivity is counted by Wallac 1450 MicroBeta.

Each percent non specific binding thus obtained is graphed as a function of compound concentration. A sigmoidal curve is used to determine 50% bindings (i.e., IC$_{50}$ values).

In this testing, most of the compounds prepared in the working examples appearing hereafter demonstrated higher affinity for ORL1-receptors than for mu-receptors.

$$IC_{50}(ORL1\text{-receptors})nM/IC_{50}(mu\text{-receptors})nM < 1.0$$

Functional Assay:

The functional activity of the compounds of this invention in each opioid receptor can be determined in 35S-GTP S binding system according to the procedures reported by L. J. Sim, R. Xiao and S. Childers *Neuroreort* Vol. 7, pp. 729–733, 1996. Each human ORL1-, mu-, kappa- and delta-receptor transfected CHO-K1 or HEK cell membranes are used. The membranes are suspended in ice-cold 20 mM HEPES buffer pH 7.4, containing 100 mM NaCl, 10 mM MgCl$_2$ and 1 mM EDTA. 0.17 mg/ml of Dithiothreitol (DTT) is added to this buffer prior to use. Membranes are incubated at 25° C. for 30 minutes with the appropriate concentration of test compounds in the presence of 5 µM GDP, 0.4 nM of 35S-GTPγS and Wheat-germ agglutinin (WGA) coated SPA bead (1.5 mg) in a 0.2 ml total volume. Basal binding is assessed in the absence of agonist, and non-specific binding is determined with 10 µM GTPγS. Radio activity is counted by Wallac 1450 MicroBeta. Some compounds of this invention prepared in Examples exhibited good ORL1 agonists activity in this assay.

Analgesic Tests:

Tail Flick Test:

Male ICR mice, 4 weeks old and weighing 19–25 g, are used. The training sessions are performed until mice can flick their tails within 4.0 sec by using Analgesia Meter MK-330A (Muromachi Kikai, Japan). Selected mice are used in this experiment. The latency time is recorded twice at 0.5, 1.0, and 2.0 h after administration of the compound. The intensity of the beam is set to 80. Cut-off time is set to 8.0 sec. A compound of this invention is subcutaneously administered 30 min before the test. The ED$_{50}$ value is defined as the dose of a compound tested which halves the tail flicking observed in a control group.

Acetic Acid Writhing Test:

Male ICR mice, 4 weeks old and weighing 21–26 g, are used. They are fasted the day before use. Acetic acid is diluted with saline to the concentration of 0.7% (v/v) and injected intraperitoneally (0.2 ml/10 g of body weight) to mice with a 26 gauge needle. A compound of this invention is dissolved in 0.1% methyl cellulose(MC)-saline and subcutaneously administered to mice 0.5 h before acetic acid injection. After the acetic acid injection, each animal is placed in a 1 L beaker and recorded by a video tape recorder. Number of writhing is counted from 5 to 15 min after acetic acid injection. The $ED_{50}$ value, defined as the dose of the compounds tested which halves the writhing is observed in the control group. Some compounds of this invention demonstrated good analgesic activity in this test.

Formalin Licking Test:

Male SD rats (80–100 g) are injected subcutaneously with a test compound dissolved in 0.1% methyl cellulose(MC)-saline or vehicle. After 30 min, 50 µl of a 2% formalin are injected into a hind paw. The number of licking the injected paw per observation period is measured from 15 to 30 min. after the injection of formalin and expressed as % inhibition compared to the respective vehicle group. This testing method is described in, for example, (1) R. L. Follenfant, et.al., Br. J. Pharmacol. 93, 85–92 (1988); (2) H. Rogers, et.al., Br. J. Pharmacol. 106, 783–789 (1992); and (3) H. Wheeler-Aceto, et al., Psychopharmacology, 104, 35–44 (1991).

The compounds of Formula (I) of this invention can be administered by conventional pharmaceutical practice via either the oral, parenteral or topical routes to mammals, for the treatment of the indicated diseases. For administration to human patient by either route, the dosage is in the range of about 0.01 mg/kg to about 3000 mg/kg body weight of the patient per day, preferably about 0.01 mg/kg to about 1000 mg/kg body weight per day administered singly or as a divided dose. However, variations will necessarily occur depending upon the weight and condition of the subject being treated, compound employed, the disease state being treated and the particular route of administration chosen.

The compounds of the present invention may be administered alone or in combination with pharmaceutically acceptable carriers by either of the above routes previously indicated, and such administration can be carried out in single or multiple doses. Generally, the compounds can be combined with various pharmaceutically acceptable carriers in the form of tablets, powders, capsules, lozenges, trochees, hard candies, powders, sprays, creams, salves, suppositories, jellies, gels, pastes, lotions, ointments, suspensions, solutions, elixirs, syrups or the like. Such pharmaceutical carriers include solvents, excipients, coating agents, bases, binders, lubricants, disintegrants, solubilizing agents, suspending agents, emulsifing agents, stabilizers, buffering agents, tonicity agents, preservatives, flavorating agents, aromatics, coloring agents and the like.

For example, the tablets can contain various excipients such as starch, lactose, glucose, microcrystalline cellulose, calcium sulfate, calcium carbonate, talc, titanium oxide and the like, coating agents such as gelatin, hydroxypropylcellulose and the like, binding agents such as gelatin, gum arabic, methylcellulose and the like, and the disintegrating agents such as starch, agar, gelatine, sodium hydrogencarbonate and the like. Additionally, lubricating agents such as magnesium stearate and talc are often very useful for tabletting purposes. Solid compositions of a similar type may also be employed as fillers in gelatine capsules; preferred materials in this connection also include lactose as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with diluents such as water, ethanol, propylene glycol, glycerin and various like combinations thereof.

In general, the therapeutically-effective compounds of this invention are present in such oral dosage forms at concentration levels ranging 5% to 70% by weight, preferably 10% to 50% by weight.

The compounds of the present invention in the form of a solution may be injected parenterlly such as intradermaly, subcutaneously, intravenously or intramuscularly. For example the solutions are sterile aqueous solutions, aqueous suspensions and an edible oil solutions. The aqueous solutions may be suitably buffered (preferably pH>8), and may contain enough salts or glucose to make the solution isotonic with blood. The aqueous solutions are suitable for intravenous injection purposes. The aqueous suspensions may contain a suitable dispersing or suspending agents such as sodium carboxymethylcellulose, methylcellulose, polyvinylpyrrolidone or gelatin. The aqueous suspensions can be used for subcutaneous or intramuscular injections. The edible oil such as cottonseed oil, sesame oil, coconut oil or peanut oil can be employed for the edible oil solutions. The oil solutions are suitable for intra-articular, intramuscular and subcutaneous injection. The preparation of all these solutions under sterile conditions is readily accomplished by standard pharmaceutical techniques well-known to those skilled in the art.

It is also possible to administer the compounds of the present invention topically when treating inflammatory conditions of the skin and this may preferably be done by way of creams, jellies, gels, pastes, ointments and the like, in accordance with standard pharmaceutical practice.

For treating a respiratory disease or symptom such as cough, a compound of this invention or a salt thereof may be administered to a mammal including a human in an aerosol formulation. The formulation may be prepared according to a method known to those skilled in the art. A compound of this invention in combination with a second agent disclosed above may also be administered to a mammal including a human by a formulation described in this specification. Those formulation may be prepared according to a method known to those skilled in the art (e.g., WO 00/06545).

Examples and Preparations

The present invention is illustrated by the following examples and preparation. However, it should be understood that the invention is not limited to the specific details of these examples and preparations. Melting points were taken with a Buchi micro melting point apparatus and is not corrected. Infrared Ray absorption spectra (IR) were measured by a Shimadzu infrared spectrometer (IR-470). $^1$H and $^{13}$C nuclear magnetic resonance spectra (NMR) were measured in $CDCl_3$ by a JEOL NMR spectrometer (JNM-GX270, 270 MHz) unless otherwise indicated and peak positions are expressed in parts per million (ppm) downfield from tetramethylsilane. The peak shapes are denoted as follows: s, singlet; d, doublet; t, triplet; m, multiplet; br, broad.

Analytical data of compounds, which can be prepared according to General Procedures A and B or were prepared in Examples hereinafter disclosed, can be taken by utilizing Waters LC-MS system (LC as 2690, ZMD as MS).

Analytical condition for LC-MS: Column YMC CombiScreen basic 4.6 mm×50 mm, Flow rate 1 mL/min.; Mobile phase 20% MeOH/80% 0.1% $HCO_2H$ in $H_2O$ programmed over 5 min to 90% MeOH/10% 0.1% $HCO_2H$ in $H_2O$. Hold for 5 min.; Wave length 220–400 nm. MS detector ApcI Cone 30 Volts.

PREPARATION 1

2-Chloro-1-(1-cyclooctylmethyl-4-piperidinyl)-1H-benzimidazole

To a stirred suspension mixture of 4-(2-keto-1-benzimidazolinyl)piperidine (17.38 g, 80 mmol) and cyclooctanecarboxaldehyde (15.39 g, 110 mmol) in $CH_2Cl_2$ (200 ml) was added $NaBH(OAc)_3$ (21 g, 99 mmol) by portions at room temperature. After overnight reaction, the reaction mixture was diluted with $CH_2Cl_2$(200 ml), washed with saturated $NaHCO_3$ solution and brine, and dried ($Na_2SO_4$). After filtration, the filtrate was concentrated to give 41.97 g of pale yellow solid. This solid was suspended in $Et_2O$ and solid was collected byfiltration to give 24.10 g of white solid. The filtrate was concentrated to give yellow solid which was suspended in $Et_2O$/hexane. The solid was collected by filtration to give 2.60 g of white solid. Total 26.7 g of desired product was obtained. A mixture of this solid(26.7 g, 78.18 mmol) and $POCl_3$ (73 ml, 788 mmol) was refluxed for 4 days. After evaporation of excess $POCl_3$, the residue was disolved in AcOEt(200 ml). Then this solution was added dropweise to a stirred mixture of $NH_4OH$(200 ml of 25% $NH_4OH$) and ice(100 g). The organic layer was separated and dried($Na_2SO_4$). After filtration, the filtrate was concentrated to give 29.05 g of dark brown viscous oil. This oil was purified by column chromatography (silica gel: 300 g, hexane/AcOEt: 4/1 as eluent) to afford 8.05 g of title compound and 18.56 g of the mixture included desired product mainly. This mixture was purified by column chromatography(silica gel: 300 g, hexane/AcOEt: 4/1 as eluent) to afford 12.44 g of desired product. Total 20.49 g(72.8%) of title compound was obtained.

$^1$H NMR ($CDCl_3$) δ 7.44–7.39(1H, m), 7.19–7.14(1H, m), 7.08(1H, dt, J=1.3, 7.4 Hz), 6.98(1H, dt, J=1.2, 7.4 Hz), 4.70–4.60(1H, m), 3.76–3.28(6H, m), 2.48–1.96(4H, m), 1.86–1.25(15H, m).

EXAMPLE 1

1-(1-Cyclooctylmethyl-4-piperidinyl)-2-4-(methylpiperazinyl)-1H-benzimidazole A mixture of 2-chloro-1-(1-cyclooctylmethyl-4-piperidinyl)-1H-benzimidazole (470 mg, 1.3 mmol) and N-methylpiperazine(260 mg, 2.6 mmol) was stirred at 120C for 6 h. Then this was purified by column chromatography (silica gel: 100 g, $CH_2Cl_2$MeOH: 10/1) to give 84 mg(14.9%) of title compound.

$^1$H NMR ($CDCl_3$) δ 7.66–7.50(2H, m), 7.20–7.10(2H, m), 4.24–4.07(1H, m), 3.30–3.24(4H, m), 3.05(2H, br.d J=11.4 Hz), 2.66–2.60(4H, m), 2.60–2.47(2H, m), 2.38(3H, s), 2.17–1.20(21H, m). MS(EI direct) m/z: 423($M^+$), 353, 338, 206(100%), 96.

This free amine(84 mg) was treated with HCl solution in MeOH(1 ml). Then this mixture was concentrated to give yellow viscous oil which was solidified by adding $Et_2O$. The solid appeared was collected by filtration to afford 89 mg of light brown solid.

Anal. Calcd for $C_{26}H_{41}N_5$—3HCl—2$H_2$): C, 54.88; H, 8.50; N, 12.31. Found: C, 55.10; H, 8.82; N, 12.04.

PREPARATION 2

2-Chloro-1-(1-cyclohexylmethyl-4-piperidinyl)-1H-benzimidazole

This was prepared according to the procedure described in preparation 1 using cyclohexanecarboxaldehyde instead of cyclooctanecarboxaldehyde. Overall yield was 19.5%.

$^1$H NMR ($CDCl_3$) δ 7.72–7.58(2H, m), 7.32–7.21(2H, m), 4.52–4.38(1H, m), 3.10–3.02(2H, m), 2.65–2.49(2H, m), 2.26–2.04(4H, m), 1.89–1.71(7H, m), 1.56–1.43(1H, m), 1.31–1.15(3H, m), 0.97–0.84(2H, m).

EXAMPLE 2

1-(1-Cyclohexylmethyl-4-piperidinyl)-2-(4-methylpiperazinyl)-1H-benzimidazole This was prepared according to the procedure described in Example 1 using 2-chloro-1-(1-cyclohexylmethyl-4-piperidinyl)-1H-benzimidazole instead of 2-chloro-1-(1-cyclooctylmethyl-4-piperidinyl)-1H-benzimidazole. Yield was 97.3%.

$^1$H NMR ($CDCl_3$) δ 7.66–7.60(1H, m), 7.55–7.49(1H, m), 7.20–7.09(2H, m), 4.21–4.08(1H, m), 3.30–3.25(4H, m), 3.10–3.01(2H, m), 2.65–2.61(4H, m), 2.56–2.49(2H, m), 2.38(3H, s), 2.21–2.16(2H, m), 2.09–2.00(4H, m), 1.86–1.66(5H, m), 1.58–1.42(1H, m), 1.29–1.14(3H, m), 0.99–0.83(2H, m). MS(ESI positive) m/z: 396(M+H)$^+$.

This free amine was converted to HCl salt, mp 206–210° C.

IR(KBr): 3385, 2930, 2671, 1595, 1458 cm$^{-1}$ Anal. Calcd for $C^{24}H^{37}N^5$—3HCl—3$H_2$O: C, 51.57; H, 8.29; N, 12.53. Found: C, 51.47; H, 8.62; N, 12.50.

PREPARATION 3

2-Chloro-1-(1-cycloheptylmethyl-4-piperidinyl)-1H-benzimidazole

This was prepared according to the procedure described in preparation 1 using cyclohepanecarboxaldehyde instead of cyclooctanecarboxaldehyde. Overall yield was 77%.

$^1$H NMR ($CDCl_3$) δ 7.70–7.60(2H, m), 7.27–7.23(2H, m), 4.54–4.37(1H, m), 3.15–2.95(2H, m), 2.67–2.47(2H, m), 2.25–2.00(4H, m), 1.95–1.35(13H, m), 1.35–1.10(2H, m).

EXAMPLE 3

1-(1-Cycloheptylmethyl-4-piperidinyl)-2-(4-methylpiperazinyl)-1H-benzimidazole This was prepared according to the procedure described in Example 1 using 2-chloro-1-(1-cycloheptylmethyl-4-piperidinyl)-1H-benzimidazole instead of 2-chloro-1-(1-cyclooctylmethyl-4-piperidinyl)-1H-benzimidazole. Yield was 73%.

$^1$H NMR ($CDCl_3$) δ 7.67–7.58(1H, m), 7.55–7.48(1H, m), 7.20–7.08(2H, m), 4.23–4.06(1H, m), 3.33–3.21(4H, m), 3.12–2.97(2H, m), 2.71–2.30(9H, m, including 3H, s, at 2.38 ppm), 2.16(2H, d, J=7.3 Hz), 2.11–1.98(2H, m), 1.90–1.36 (13H, m), 1.26–1.07(2H, m). MS(EI direct) m/z: 409(M)$^+$, 327, 227, 163, 99.

PREPARATION 4

1-(1-Cyclopentylmethyl-4-piperidinyl)-1,3-dihydro-2H-benzimidazole-2-one

To a stirred solution of 4-(2-keto-1-benzimidazolinyl) piperidine(217.3 mg, 1 mmol) and $Et_3N$(15.39 g, 110 mmol) in $CH_2Cl_2$(5 ml) was added cyclopentanecarbonyl chloride (146 ml, 1.2 mmol) dropwise at 0° C. After 2 h stirring, the reaction mixture was diluted with $CH_2Cl_2$, washed with saturated $NaHCO_3$ solution and brine, and dried($Na_2SO_4$). After filtration, the filtrate was concentrated. The residue was purified by preparative TLC (1 mm thick plate×2, CH$_2$Cl$_2$/MeOH:12/1) to give 291 mg (93%) of amide compound as white solid. To a stirred suspension of LiAlH$_4$(53 mg, 1.394 mmol) in THF(5 ml) was added a solution of the above amide derivative(291 mg, 0.929 mmol) in THF(5 ml) at −78° C. The reaction mixture was stirred at −78° C. to −20° C. for 4 h. The reaction mixture was quenched with Na$_2$SO$_4$-10H$_2$O and diluted with CH$_2$Cl$_2$. The solid appeared was removed by filtration and the filtrate was concentrated to give oil, which was purified by preparative TLC (1 mm thick plate×2, CH$_2$Cl$_2$/MeOH:12/1) to give 202 mg (73%) as colorless amorphous solid.

$^1$H NMR (CDCl$_3$) δ 10.30 (1H, br. s), 7.34–7.26(1H, m), 7.16–7.00(3H, m), 4.45–4.30(1H, m), 3.18–3.06(2H, m), 2.60–2.40(2H, m), 2.35(2H, d, J=7.2 Hz), 2.22–2.00(3H, m), 1.87–1.45(8H, m), 1.35–1.15(2H, m).

EXAMPLE 4

1-(1-Cyclopentylmethyl-4-piperidinyl)-2-(4-methylpiperazinyl)-1H-benzimidazole The mixture of 1-(1-cyclopentylmethyl-4-piperidinyl)-1,3-dihydro-2H-benzimidazole-2-one(202 mg) and POCl$_3$(5 ml) was heated at 120° C. for 2 h. After cooling down to room temperature, the reaction mixture was poured into NH$_4$OH solution, and extracted with CH$_2$Cl$_2$. The extracts combined were washed with water, and dried (Na$_2$SO$_4$). After filtration, the filtrate was concentrated to give oil, which was purified by preparative TLC (1 mm thick plate×2, CH$_2$Cl$_2$/MeOH:15/1) to give 148 mg (69%) of 2-chloro-1-(1-cyclopentylmethyl-4-peridinyl)-1H-benzimidazole as colorless amorphous solid. To a solution of 2-chloro-1-(1-cyclopentylmethyl-4-piperidinyl)-1H-benzimidazole(148 mg, 0.466 mmol) in MeOH(5 ml) was added N-methylpiperazine(1 ml) and the resulting mixture was heated at 120° C. in a sealed tube for 2 days. After concentration, the residue was purified by preparative TLC (1 mm thick plate×2, CH$_2$Cl$_2$/MeOH:12/1, 2 developed) to give 161 mg of colorless amorphous solid. This was purified again by column chromatography(basic silica gel: 50 g; CH$_2$Cl$_2$/MeOH:200/1 to 50/1) to afford 52 mg (29%) of title compound as colorless amorphous solid.

$^1$H NMR (CDCl$_3$) δ 7.66–7.58(1H, m), 7.57–7.49(1H, m), 7.20–7.08(2H, m), 4.22–4.08(1H, m), 3.32–3.24(4H, m), 3.16–3.07(2H, m), 2.66–2.30(11H, m, including 3H, s, at 2.38 ppm, and 2H, d, J=7.3 Hz at 2.33 ppm), 2.18–2.00(3H, m), 1.96–1.50(8H, m), 1.34–1.16(2H, m). MS(EI direct) m/z: 381(M)$^+$, 311, 296, 217, 164(100%), 96.

PREPARATION 5

2-Chloro-1-(1-benzyl-4-piperidinyl)-1H-benzimidazole

This was prepared according to the procedure described in Preparation 1 using benzaldehyde instead of cyclooctanecarboxaldehyde. Total yield was 23.1%.

$^1$H NMR (CDCl$_3$) δ 7.70–7.60(2H, m), 7.40–7.20(7H, m), 4.52–4.42(1H, m), 3.61(2H, s), 3.20–3.07(2H, m), 2.65–2.50(2H, m), 2.25–2.15(2H, m), 1.90–1.85(2H, m).

EXAMPLE 5

1-(1-Benzyl-4-piperidinyl)-2-(4-methylpiperazinyl)-1H-benzimidazole

This was prepared according to the procedure described in Example 1. Total yield was 76%.

$^1$H NMR (CDCl$_3$) δ 7.64–7.50(2H, m), 7.40–7.10(7H, m), 4.24–4.14(1H, m), 3.59(2H, s), 3.30–3.24(4H, m), 3.12–3.05(2H, m), 2.70–2.50(6H, m), 2.38(3H, s), 2.20–2.13(2H, m), 1.80–1.75(2H, m). MS(EI direct) m/z: 389(M$^+$), 306, 217, 172, 91(100%).

PREPARATION 6

2-(4-Methylpiperazinyl)-1-(4-piperidinyl)-1H-benzimidazole

A suspension mixture of 1-(1-benzyl-4-piperidinyl)-2-(4-methylpiperazinyl)-1H-benzimidazole (4.62 g, 11.86 mmol) and Pd(OH)$_2$/C (2.35 g) in MeOH(100 ml) was stirred under hydrogen atmosphere at room temperature for 23 h. The catalyst was removed by filtration and the filtrate was concentrated to give 3.10 g (87%) of title compound as white solid.

$^1$H NMR (CDCl$_3$) δ 7.65–7.57(2H, m), 7.20–7.10(2H, m), 4.40–4.25(1H, m), 3.50–3.40(2H, m), 3.40–3.25(4H, m), 2.90–2.82(2H, m), 2.80–2.50(7H, m), 2.40(3H, s), 1.91–1.85(2H, m).

EXAMPLE 6

1-(1-Cyclobutylmethyl-4-piperidinyl)-2-(4-methylpiperazinyl)-1H-benzimidazole A mixture of 2-(4-methylpiperazinyl)-1-(4-piperidinyl)-1H-benzimidazole (300 mg, 1 mmol), K$_2$CO$_3$ (165.9 mg, 1.2 mmol), and (bromomethyl)cyclobutane (178.8 mg, 1.2 mmol) in DMF (4 ml) was stirred at room temperature for 17 h. Then K$_2$CO$_3$ (110 mg, 0.8 mmol), and (bromomethyl)cyclobutane (119 mg, 0.8 mmol) were added to the reaction mixture. After 16 h stirring, the reaction mixture was poured into water and extracted with CH$_2$Cl$_2$. The extracts combined were dried (MgSO4), filtered, and concentrated in vacuo to give 369 mg of oil which was purified by preparative TLC (1 mm thick plate, CH$_2$Cl$_2$/MeOH:10/12 developped) to afford 147.6 mg (40%) of title compound as light brown solid.

$^1$H NMR (CDCl$_3$) δ 7.66–7.50(2H, m), 7.20–7.08(2H, m), 4.25–4.08(1H, m), 3.35–3.20(4H, m), 3.10–2.80(3H, m), 2.70–2.45(8H, m), 2.38(3H, s), 2.20–2.05(4H, m), 2.00–1.65(6H, m). MS(EI direct) m/z: 367(M$^+$), 341, 311, 282, 256, 217, 150(100%), 96.

The chemical structures of the compounds of Formula (I), prepared in Examples 1 to 6, are summarized in Table 1.

TABLE 1

(I)

| Ex. # | R$^1$ | R$^2$ | (R$^3$)(R$^4$)N— | R$^5$ |
|---|---|---|---|---|
| 1 | H | H | 4-methyl-piperazin-1-yl | Cyclooctyl |
| 2 | H | H | 4-methyl-piperazin-1-yl | Cyclohexyl |
| 3 | H | H | 4-methyl-piperazin-1-yl | Cycloheptyl |
| 4 | H | H | 4-methyl-piperazin-1-yl | Cyclopentyl |
| 5 | H | H | 4-methyl-piperazin-1-yl | Phenyl |
| 6 | H | H | 4-methyl-piperazin-1-yl | Cyclobutyl |

Also, compounds of formula (I), wherein both R$^1$ and R$^2$ are hydrogen and R$^5$ is cyclooctyl, were prepared according to General Procedure A or B described in this specification using appropriate starting materials. Those compounds are summarized following table.

TABLE 2

| Example # | General Procedure | (R³)(R⁴)N— | M + 1 (APCI) |
|---|---|---|---|
| 7 | A | Piperidino | 409 |
| 8 | A | 3-hydroxy-pyrrolidin-1-yl | 412 |
| 9 | A | 3-hydroxymethyl-piperidino | 440 |
| 10 | A | Morpholino | 412 |
| 11a | A | 4-(2-aminoethyl)-piperazin-1-yl | 454 |
| 11b | A | 2-(piperazin-1-yl)ethylamino | 454 |
| 12 | A | Cyclohexylamino | 424 |
| 13 | A | 2-(N,N-dimethylamino)ethylamino | 412 |
| 14 | A | Cyclopropylamino | 410 |
| 15 | A | (2-pyridinyl)methylamino | 432 |
| 16 | A | 3-chloroanilino | 451 |
| 17 | A | (2-furyl)methylamino | 422 |
| 18 | A | (R)-(+)-1-phenylethylamino | 446 |
| 19 | A | 2-(2-indolyl)ethylamino | 484 |
| 20 | B | (R)-(+)-2-hydroxy-1-phenylethylamino | 462 |
| 21 | B | 2-hydroxy-2-phenylethylamino | 462 |
| 22 | B | 3-(2-pyrrolidinon-1-yl)propylamino | 467 |
| 23 | B | 4-phenylpiperazinyl | 487 |
| 24 | B | 4-acetylpiperazinyl | 453 |
| 25 | B | 4-[4-(N,N-dibenzylamino)piperidino]-piperidino | 688 |
| 26 | B | 1-{[1-(1-pyrrolidinylmethyl)-cyclopentyl]methyl}piperazinyl | 576 |
| 27 | B | 2-hydroxyethylamino | 386 |
| 28 | B | 2-phenylethylamino | 446 |
| 29 | B | 3-(imidazol-1-yl)propylamino | 450 |
| 30 | B | 3-methoxypropylamino | 414 |
| 31 | B | 2-phenoxyethylamino | 462 |
| 32 | B | 2-(R)-(–)-hydroxypropylamino | 400 |
| 33 | | azocan-1-yl | 437.5 |
| 34 | | pyrrolidinyl | 395.5 |
| 35 | | 2-(S)-(hydroxymethyl)pyrroridinyl | 425.5 |
| 36 | | 4-(1,3-benzodioxol-5-ylmethyl)-piperazinyl | 544.5 |
| 37 | | 1,2,3,6-tetrahydropyridin-1-yl | 407.5 |
| 38 | | 4-(2-metoxyphenyl)piperazinyl | 516.6 |
| 39 | | 4-(4-fluorophenyl)piperazinyl | 504.6 |
| 40 | | 4-benzylpiperazinyl | 500.3 |
| 41 | | 4-(2-hydroxyethyl)piperazinyl | 454.5 |
| 42 | | 1,4-dioxa-8-azaspiro[4.5]decan-8-yl | 467.5 |
| 43 | | piperidino | 409.5 |
| 44 | | 3-(ethoxycarbonyl)piperidino | 481.5 |
| 45 | | 3-methylpiperidino | 423.5 |
| 46 | | 3,5-dimethylpiperidino | 437.5 |
| 47 | | 3-(hydroxymethyl)piperidino | |
| 48 | | 4-hydroxy-4-phenylpiperidino | 501.5 |
| 49 | | 4-methylpiperidino | 423.5 |
| 50 | | 4-benzylpiperizino | |
| 51 | | decahydroisoquinolin-2-yl | 463.5 |
| 52 | | 1,2,3,4-tetrahydroisoquinolin-2-yl | 457.3 |
| 53 | | homopiperidino | 423.5 |
| 54 | | 2-(S)-(methoxymethyl)pyrroridinyl | 439.3 |
| 55 | | 2-(S)-(pyrrolidinylmethyl)pyrroridinyl | 478.5 |
| 56 | | 4-(2-fluorophenyl)piperazinyl | 504.4 |
| 57 | | 4-methylhomopiperazinyl | 438.5 |
| 58 | | trans-1-cinnamylpiperazinyl | 526.5 |
| 59 | | 2-(S)-(hydroxymethyl)pyrroridinyl | 425.5 |
| 60 | | 4-t-buthoxycarbonylpiperazinyl | 510.4 |
| 61 | | 4-benzyloxycarbonylpiperazinyl | 544.5 |
| 62 | | 3,5-dimethylmorpholino | 439.5 |
| 63 | | 2-methyl-5-ethylpiperidino | 451.5 |
| 64 | | 4-hydroxymethylpiperidino | 439.5 |
| 65 | | 4-(2-metoxyphenyl)piperidino | 515.5 |
| 66 | | N-methyl-N-2-hydroxy-2-phenylethyl-amino | 475.5 |
| 67 | | 3-carbamoylpiperidino | 452.5 |
| 68 | | N-methyl-N-propylamino | 397.3 |
| 69 | | N-methyl-N-3-hydroxy-3-phenylpropyl-amino | 489.5 |
| 70 | | 2-(S)-methoxymethylpyrrolidinyl | |
| 71 | | 3-t-buthoxycarbonylaminopyrrolidinyl | 510.1 |
| 72 | | N-methyl-N-(1-naphthyl)methylamino | 495.5 |
| 73 | | 4-(4-trifluoromethylpyridin-2-yl)-piperazinyl | 555.5 |
| 74 | | 4-(3-trifluoromethylpyridin-2-yl)-piperazinyl | 555.5 |
| 75 | | 4-(3-chloro-5-trifluoromethylpyridin-2-yl)piperazinyl | 589.5 |
| 76 | | 4-(2-trifluoromethylquinolin-4-yl)-piperazinyl | 605.6 |
| 77 | | 1,3,3-trimethyl-6-azabicyclo[3.2.1]-octan-6-yl | 477.4 |
| 78 | | N-n-hexyl-N-methylamino | 439.4 |
| 79 | | N-2-(N,N-dimethylaminoethyl)-N-methylamino | 426.3 |
| 80 | | 3-(N,N-diethylaminocarbonyl)-piperidino | 508.4 |
| 81 | | 4-(4-fluorophenyl)piperazin-1-yl | 504.4 |
| 82 | | 4-(2-nitro-4-trifluorophenyl)piperazin-1-yl | 599.4 |
| 83 | | 3-pyrrolin-1-yl | |
| 84 | | 4-formylpiperazin-1-yl | 438.4 |
| 85 | | 1,3,4,6,7,8-hexahydro-2H-pyrimido-[1,2-a]pyrimidin-1-yl | 463.4 |
| 86 | | 4-acetylpiperazin-1-yl | |
| 87 | | 4-ethylpiperazin-1-yl | 438.4 |
| 88 | | 4-ethoxy-3-hydroxyethyl-piperazin-1-yl | 498.4 |
| 89 | | 2,3-dihydro-1H-benzo[de]isoquinolin-2-yl | 493.4 |
| 90 | | N-(2-hydroxyethyl)-N-n-butylamino | 441.3 |
| 91 | | N,N-bis(2-pyridinylmethyl)amino | 523.4 |
| 92 | | N-(1-benzyl-3-pyrrolidinyl)-N-methylamino | 514.4 |
| 93 | | 2,6-dimethylmorpholino | 439.5 |
| 94 | | 4-(2-ethoxyphenyl)piperazin-1-yl | 530.5 |
| 95 | | 4-(3,4-dichlorophenyl)piperazin-1-yl | 554.5 |
| 96 | | 4-(3,5-dimethylphenyl)piperazin-1-yl | 514.5 |
| 97 | | 4-benzhydrylpiperazin-1-yl | 576.5 |
| 98 | | 4-(2-chlorophenyl)piperazin-1-yl | 520.5 |
| 99 | | N-cyclohexyl-N-methylamino | 437.5 |
| 100 | | N-isobutyl-N-methylamino | 411.3 |
| 101 | | N-(2-hydroxyethyl)-N-n-pentylamino | 455.4 |
| 102 | | N-(1,3-dioxolan-2-ylmethyl)-N-methyl-amino | 441.3 |
| 103 | | N-benzyl-N-methylamino | 445.3 |
| 104 | | 2,4-dimethyl-4,5-dihydro-1H-imidazol-1-yl | 422.3 |
| 105 | | N-(2-phenylethyl)-N-methylamino | 459.3 |
| 106 | | N-(1-methylpiperidin-4-yl)methyl-amino | 452.3 |
| 107 | | L-prolylamino | 438.3 |
| 108 | | N-benzyl-N-2-hydroxyethylamino | 475.3 |
| 109 | | N-n-Butyl-N-4-hydroxybutylamino | 469.3 |
| 110 | | N-(2-hydroxyphenyl)methyl-N-methyl-amino | 461.1 |
| 111 | | 4-ethoxycarbonylpiperazin-1-yl | 482.3 |
| 112 | | N-2-(4-ethoxy-3-methoxyphenyl)-ethylamino | |
| 113 | | N-3-(N,N-dimethylamino)-2,2-dimethylpropylamino | 454.3 |
| 114 | | N-3-ethoxylpropylamino | 427.3 |
| 115 | | N-(1-methyl-2-pyrrolidinyl)ethyl-amino | 452.3 |
| 116 | | N-4-phenylbutylamino | 473.4 |
| 117 | | N-2-(4-fluorophenyl)ethylamino | 463.3 |
| 118 | | N-ethoxycarbonyl-N-phenylamino | |
| 119 | | N-(1-ethylpyrrolidin-2-yl)methyl-amino | 452.3 |
| 120 | | N-[(1S, 2R, 5S)-6,6-dimethyl-bicyclo[3.1.1]hept-2-yl]methylamino | 477.4 |
| 121 | | N-(1,3-dioxolan-2-yl)ethylamino | 441.3 |
| 122 | | N-(4-methylcyclohexan-1-yl)amino | 437.5 |
| 123 | | N-(2-ethoxy)ethyl-N-methylamino | 413.3 |
| 124 | | N-3-methylcyclohexylamino | 437.3 |
| 125 | | (R)-(–)-tyetrahydrofurfurylamino | 425.3 |
| 126 | | N-(2,2-dimethoxy)ethylamino | 429.2 |
| 127 | | exo-2-norbornanamino | 435.3 |

TABLE 2-continued

| Example # | General Procedure | (R³)(R⁴)N— | M + 1 (APCI) |
|---|---|---|---|
| 128 | | N-(3,3-dimethylbutyl)amino | 425.3 |
| 129 | | N-(2-(S)-methylbutyl)amino | 411.3 |
| 130 | | N-2-(3,4-dimethoxyphenyl)ethyl-amino | 519.3 |
| 131 | | N,N-bis-2-(N',N'-diethylaminoethyl)-amino | 539.3 |
| 132 | | N-2-methylthioethylamino | 415.2 |
| 133 | | N-4-trifluoromethoxybenzylamino | 515.3 |
| 134 | | N-2-methoxybenzylamino | 461.3 |
| 135 | | (3S)-2-azepanon-3-ylamino | 452.3 |
| 136 | | 3,4,5-trimethoxybenzylamino | 521.2 |
| 137 | | (1S)-1-(1naphthyl)ethylamino | 495.2 |
| 138 | | (1S)-1-(1naphthyl)ethylamino | 495.2 |
| 139 | | N-3-(2-methylpiperidino)propylamino | 480.4 |
| 140 | | (3S)-N-(1-benzylpyrrolidin-3-yl)-amino | 500.4 |
| 141 | | (3R)-N-(1-benzylpyrrolidin-3-yl)-amino | 500.4 |
| 142 | | N-2-(3,5-dimethoxyphenyl)ethylamino | 505.3 |
| 143 | | 3-ethoxycarbonylbicyclo[3.1.1]-heptan-2-ylamino | |
| 144 | | 6-ethoxycarbonyl-3-cyclohexen-1-yl-amino | 493.3 |

What is claimed is:
1. A compound of the following formula:

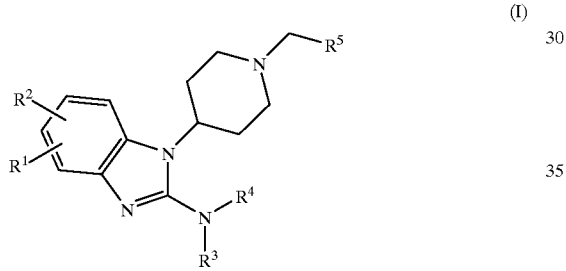

(I)

or a salt thereof, wherein
$R^1$ and $R^2$ are independently selected from hydrogen; halo; hydroxy; $(C_1-C_4)$alkyl; $(C_2-C_4)$alkenyl; $(C_2-C_4)$alkynyl; halo $(C_1-C_4)$alkyl; $(C_1-C_4)$alkoxy; $(C_1-C_4)$alkylsulfonyl; $(C_1-C_4)$alkyl-C(=O)—; carboxy; $(C_1-C_4)$alkyl-C(=O)O—; amino; $NH_2$—C(=O)—; $(C_1-C_4)$alkyl-C(=O)—NH—; $(C_1-C_4)$alkyl-$SO_2$—NH—; phenyl and naphthyl;
$R^3$ and $R^4$ are independently selected from halo$(C_1-C_{10})$alkyl;
$(C_1-C_6)$alkyl substituted with one to two substituents independently selected from hydroxy, $(C_1-C_4)$alkoxy, $(C_1-C_4)$alkyl-S—, phenoxy, amino, oxo, mono[$(C_1-C_4)$alkyl]amino, di[$(C_1-C_4)$alkyl]amino, N-[$(C_7-C_9)$cycloalkyl-$(C_1-C_4)$alkyl]-N-$(C_1-C_4)$alkyl-amino, $(C_1-C_4)$alkoxy-C(=O)—, aryl selected from phenyl and naphthyl wherein the aryl is optionally substituted with one to three substituents independently selected from halo, hydroxy, $(C_1-C_4)$alkoxy, and trifluoro$(C_1-C_4)$alkoxy, and heterocyclyl selected from pyrrolidyl and piperidinyl wherein the heterocyclyl is optionally substituted with $(C_1-C_4)$alkyl;
$(C_3-C_8)$cycloalkyl optionally substituted with $(C_1-C_4)$alkyl;
$(C_3-C_8)$cycloalkenyl optionally substituted with $(C_1-C_4)$alkoxy-C(=O)—;

5- to 6-membered heterocyclyl, 5- to 6-membered heterocyclyl-(C=O)— and 5-to 6-membered heterocyclyl-$(C_1-C_4)$alkyl wherein each heterocyclyl contains in the ring one to three heteroatoms independently selected from oxygen, nitrogen and sulfur, is optionally fused to a phenyl ring, and is optionally substituted with one to two substituents independently selected from halo, $(C_1-C_4)$alkyl, benzyl and oxo;
phenyl optionally substituted with one to three substituents independently selected from halo, $(C_1-C_4)$alkyl, halo$(C_1-C_4)$alkyl and $(C_1-C_4)$alkoxy; and
5- to 6-membered heteroaryl-$(C_1-C_4)$alkyl wherein said heteroaryl contains one to four ring atoms independently selected from oxygen, nitrogen and sulfur and is optionally fused to a phenyl ring; or
$R^3$ and $R^4$, together with the nitrogen atom to which they are attached, form a fully saturated, partially saturated or fully unsaturated 5- to 8-membered nitrogen containing heterocyclic ring wherein said heterocyclic ring optionally contains in the ring one or two additional heteroatoms independently selected from nitrogen, oxygen and sulfur, optionally contains in the ring a group $CR^6R^7$ wherein $R^6$ and $R^7$ taken together form an oxo group or a cyclic acetal, and is optionally fused to a phenyl, naphthalene or $(C_5-C_8)$cycloalkyl ring, and optionally substituted with one to two substituents independently selected from halo; $(C_1-C_4)$alkyl; halo $(C_1-C_4)$alkyl; $(C_1-C_4)$alkoxy; hydroxy; carbonyl; benzhydryl; hydroxy-$(C_1-C_4)$alkyl; $(C_1-C_4)$alkoxy-$(C_1-C_4)$alkyl-; amino; amino-$(C_1-C_4)$alkyl-amino; mercapto; $(C_1-C_4)$alkoxy-C(=O)—; pyrrolidino-$(C_1-C_4)$alkyl, amino-C(=O)—; $(C_1-C_4)$alkyl-C(=O)—; $(C_1-C_4)$alkoxy-C(=O)—amino-; piperidinyl optionally substituted with one or two substituents independently selected from amino, mono[$(C_1-C_4)$alkyl]amino, di[$(C_1-C_4)$alkyl]amino-, benzylamino and di-(benzyl)amino; phenyl optionally substituted with one to three substituents selected from halo and $(C_1-C_4)$alkoxy; phenyl-$(C_1-C_4)$alkyl; phenyl-$(C_1-C_4)$alkenyl; phenyl-$(C_1-C_4)$alkoxy-C(=O)—; 1,3-benzodioxolyl-$(C_1-C_4)$alkyl-; trifluoromethyl; nitro; pyridyl optionally substituted with one to three substituents independently selected from halo and trifluoromethyl; quinolinyl optionally substituted with one to three substituents independently selected from halo and trifluoromethyl; pyrrolidinyl-$(C_1-C_4)$alkyl and pyrrolidinyl-$(CH_2)_m$—$CR^8R^9$—$(CH_2)_n$— wherein m and n are independently 1, 2, 3 or 4, and $R^8$ and $R^9$, taken together with the carbon atom to which they are attached, form $(C_3-C_6)$cycloalkyl; and
$R^5$ is phenyl or $(C_4-C_{11})$cycloalkyl optionally substituted with one to three substituents independently selected from the group consisting of hydrogen, halo, hydroxy, $(C_1-C_4)$alkyl, halo $(C_1-C_4)$alkyl, $(C_1-C_4)$alkoxy, $(C_1-C_4)$alkylsulfonyl, $(C_1-C_4)$alkyl-C(=O)—, carboxy, $(C_1-C_4)$alkyl-C(=O)O—, amino, $NH_2$-C(=O)—, $(C_1-C_4)$alkyl-C(=O)—NH—, $(C_1-C_4)$alkyl-$SO_2$—NH—, phenyl and naphthyl.
2. A compound according to claim 1, wherein $R^1$ and $R^2$ are independently selected from hydrogen, halo, $(C_1-C_4)$alkyl, $(C_2-C_4)$alkenyl, $(C_2-C_4)$alkynyl, halo$(C_1-C_4)$alkyl and $(C_1-C_4)$alkoxy;
$R^3$ and $R^4$ are independently selected from halo$(C_1-C_{10})$alkyl; $(C_1-C_6)$alkyl substituted with one to two substituents independently selected from hydroxy, $(C_1-C_4)$ alkoxy, phenoxy, amino, mono[$(C_1-C_4)$alkyl]amino, di[$(C_1-C_4)$alkyl]amino, phenyl and naphthyl; $(C_3-C_8)$ cycloalkyl; 5- to 6-membered heterocyclyl-$(C_1-C_4)$ alkyl wherein said heterocyclyl is selected from pyrrolidino, piperidino, morpholino, piperazinyl and homopiperazinyl and optionally substituted with one to two substituents independently selected from halo and oxo; phenyl optionally substituted with one to three substituents independently selected from halo, $(C_1-C_4)$ alkyl, halo$(C_1-C_4)$alkyl and $(C_1-C_4)$alkoxy; and heteroaryl-$(C_1-C_4)$alkyl wherein said heteroaryl is selected from furyl, thiophenyl, pyrrolyl, pyrazolyl, imidazolyl, triazolyl, tetrazolyl, isoxazolyl, oxazolyl, thiazolyl, isothiazolyl, oxadiazolyl, pyridyl, pyridazinyl, pyrimidinyl, pyrazinyl, triazinyl, indolyl, benzofuranyl, benzothiophenyl, isoindolyl and isobenzofuranyl; or $R^3$ and $R^4$, together with the nitrogen atom to which they are attached, form a fully saturated, partially saturated or fully unsaturated heterocyclic ring wherein said heterocyclic ring is selected from pyrrolidinyl, piperidinyl, morpholinyl, piperazinyl, homopiperidinyl, homopiperazinyl, azocanyl, tetrahydropyridinyl, octahydroquinolyl, quinolyl, tetrahydroquinolyl, isoquinolyl, tetrahydroisoquinolyl and octahydroisoquinolyl and optionally substituted with one to two substituents independently selected from halo; $(C_1-C_4)$alkyl; halo$(C_1-C_4)$alkyl; $(C_1-C_4)$ alkoxy; hydroxy; hydroxy-$(C_1-C_4)$alkyl; $(C_1-C_4)$ alkoxy-$(C_1-C_4)$alkyl-; amino; amino-$(C_1-C_4)$alkyl-; mercapto; $(C_1-C_4)$alkoxy-$(C=O)$—; pyrrolidino-$(C_1-C_4)$alkyl amino-$(C=O)$—; $(C_1-C_4)$alkyl-$(C=O)$—; $(C_1-C_4)$alkoxy-$(C=O)$—amino-; piperidinyl optionally substituted with one or two substituents independently selected from amino, mono[$(C_1-C_4)$ alkyl]amino, di[$(C_1-C_4)$alkyl]amino-, benzylamino and di-(benzyl)amino; phenyl optionally substituted with one to three substituents selected from halo and $(C_1-C_4)$alkoxy; phenyl-$(C_1-C_4)$alkyl; phenyl-$(C_1-C_4)$ alkenyl; phenyl-$(C_1-C_4)$alkoxy-$(C=O)$—; 1,3-benzodioxolyl-$(C_1-C_4)$alkyl-; pyridyl optionally substituted with one to three substituents independently selected from halo and trifluoromethyl; quinolinyl optionally substituted with one to three substituents independently selected from halo and trifluoromethyl; pyrrolidinyl-$(C_1-C_4)$alkyl and pyrrolidinyl-$(CH_2)_m$—$CR^8R^9$—$(CH_2)_n$—, wherein m and n are independently 1, 2, 3 or 4, and $R^8$ and $R^9$, taken together with the carbon atom to which they are attached, form $(C_3-C_6)$ cycloalkyl; and $R^5$ is unsubstituted $(C_4-C_{11})$cycloalkyl.

3. A compound according to claim 2, wherein $R^1$ and $R^2$ are independently selected from hydrogen, halo, $(C_1-C_4)$alkyl, $(C2-C_4)$alkenyl, $(C_2-C_4)$alkynyl, halo$(C_1-C_4)$alkyl and $(C_1-C_4)$alkoxy;

$R^3$ and $R^4$ are independently selected from halo$(C_1-C_{10})$ alkyl; $(C_1-C_6)$alkyl substituted with one to two substituents independently selected from hydroxy, $(C_1-C_4)$ alkoxy, phenoxy, amino, mono[$(C_1-C_4)$alkyl]amino, di[$(C_1-C_4)$alkyl]amino, phenyl and naphthyl; $(C_3-C_8)$ cycloalkyl; heterocyclyl-$(C_1-C_4)$alkyl wherein said heterocyclyl is selected from pyrrolidino, piperidino, morpholino, piperazinyl and homopiperazinyl and optionally substituted with one to two substituents independently selected from halo and oxo; phenyl optionally substituted with one to three substituents independently selected from halo, $(C_1-C_4)$alkyl, halo $(C_1-C_4)$alkyl and $(C_1-C_4)$alkoxy; and heteroaryl-$(C_1-C_4)$alkyl wherein said heteroaryl is selected from furyl, thiophenyl, pyrrolyl, pyrazolyl, imidazolyl, triazolyl, tetrazolyl, isoxazolyl, oxazolyl, thiazolyl, isothiazolyl, oxadiazolyl, pyridyl, pyridazinyl, pyrimidinyl, pyrazinyl, triazinyl, indolyl, benzofuranyl, benzothiophenyl, isoindolyl and isobenzofuranyl; and $R^5$ is unsubstituted $(C4-C_{11})$cycloalkyl.

4. A compound according to claim 3 selected from $R^1$ and $R^2$ are both hydrogen;

$R^3$ and $R^4$ are independently selected from $(C_1-C_6)$alkyl substituted with one to three substituents independently selected from hydroxy, $(C_1-C_4)$alkoxy, phenoxy, di-[$(C_1-C_4)$alkyl]amino, phenyl and naphthyl; $(C_3-C_8)$ cycloalkyl; heterocyclyl-$(C_1-C_4)$alkyl wherein said heterocyclyl is selected from pyrrolidino, piperidino, morpholino and piperazinyl and optionally substituted with one to two substituents independently selected from halo and oxo; phenyl optionally substituted with one to three halo; and heteroaryl-$(C_1-C_4)$alkyl wherein said heteroaryl is selected from furyl, pyridyl and indolyl; and $R^5$ is unsubstituted $(C_5-C_8)$cycloalkyl.

5. A compound according to claim 4 wherein $R^1$ and $R^2$ are both hydrogen; $R^3$ and $R^4$ are independently $(C_1-C_6)$alkyl substituted with one to three substituents independently selected from hydroxy, $(C_1-C_4)$ alkoxy, phenoxy, di-[$(C_1-C_4)$alkyl]amino, phenyl and naphthyl; and $R^5$ is unsubstituted $(C_5-C_8)$cycloalkyl.

6. A compound according to claim 2, wherein $R^1$ and $R^2$ are independently selected from hydrogen, halo, $(C_1-C_4)$alkyl, $(C_2-C_4)$alkenyl, $(C_2-C_4)$alkynyl, halo$(C_1-C_4)$alkyl and $(C_1-C_4)$alkoxy;

$R^3$ and $R^4$, together with the nitrogen atom to which they are attached, form a 5- to 6-membered heterocyclic ring selected from pyrrolidino, piperidino, morpholino, piperazinyl and homopiperazinyl, and optionally substituted with one to two substituents independently selected from $(C_1-C_4)$alkyl, hydroxy, hydroxy-$(C_1-C_4)$ alkyl, amino, amino-$(C_1-C_4)$alkyl and piperidinyl optionally substituted with one or two substituents independently selected from amino, benzylamino, di-(benzyl)amino, $(C_1-C_4)$alkyl-$C(=O)$— and pyrrolidino-$(CH_2)_m$—$CR^7R^8$—$(CH_2)_n$—, wherein m and n are independently 1, 2, 3 or 4, and $R^7$ and $R^8$, taken together with the carbon atom to which they are attached, form $(C_3-C_6)$cycloalkyl; and $R^1$ is unsubstituted $(C_4-C_{11})$cycloalkyl.

7. A compound according to claim 6, wherein $R^1$ and $R^2$ are both hydrogen;

$R^3$ and $R^4$, together with the nitrogen atom to which they are attached, form a 5- to 6-membered heterocyclic ring selected from pyrrolidino, piperidino, morpholino and piperazinyl, and optionally substituted with one to two substituents independently selected from $(C_1-C_4)$alkyl, hydroxy, hydroxy-$(C_1-C_4)$alkyl, amino, amino-$(C_1-C_4)$alkyl, $(C_1-C_4)$alkyl-$C(=O)$— and piperidinyl optionally substituted with one or two substituents independently selected from amino, benzylamino, di- (benzyl)amino and pyrrolidino-$(CH_2)_m$—$CR^7R^8$—$(CH_2)_n$—, wherein m and n are independently 1, 2, 3 or 4, and $R^7$ and $R^8$, taken together with the carbon atom to which they are attached, form $(C_3-C_6)$cycloalkyl; and $R^5$ is unsubstituted $(C_5-C_8)$cycloalkyl.

8. A compound of claim 7, wherein $R^1$ and $R^2$ are both hydrogen; $R^3$ and $R^4$, together with the nitrogen atom to which they are attached, form piperazinyl substituted with $(C_1-C_4)$alkyl; and $R^5$ is unsubstituted $(C_5-C_8)$cycloalkyl.

9. A compound of claim 8 selected from the group consisting of 1-(1-cyclooctylmethyl-4-piperidinyl)-2-(4-methylpiperazinyl)-1H-benzimidazole; 1-(1-cyclohexylmethyl-4-piperidinyl)-2-(4-methylpiperazinyl)-1H-benzimidazole; and 1-(1-Cycloheptylmethyl-4-piperidinyl)-2-(4-methylpiperazinyl)-1H-benzimidazole; or a salt thereof.

10. A pharmaceutical composition useful as analgesics comprising an amount of a compound of claim 1, or a pharmaceutically acceptable salt thereof that is effective in the use in a mammal including a human, and a pharmaceutically acceptable carrier.

* * * * *